(12) United States Patent
Wang et al.

(10) Patent No.: US 11,873,709 B2
(45) Date of Patent: Jan. 16, 2024

(54) LOG BASED DIAGENETIC ROCK TYPING AND SWEET SPOT IDENTIFICATION FOR TIGHT GAS SANDSTONE RESERVOIRS

(71) Applicant: Saudi Arabian Oil Company, Dhahran (SA)

(72) Inventors: Weihua Wang, Dhahran (SA); Yunsheng Li, Dhahran (SA)

(73) Assignee: Saudi Arabian Oil Company, Dhahran (SA)

(*) Notice: Subject to any disclaimer, the term of this patent is extended or adjusted under 35 U.S.C. 154(b) by 513 days.

(21) Appl. No.: 17/064,896

(22) Filed: Oct. 7, 2020

(65) Prior Publication Data
US 2022/0106866 A1   Apr. 7, 2022

(51) Int. Cl.
*E21B 47/003* (2012.01)
*E21B 43/26* (2006.01)
*G01N 33/24* (2006.01)

(52) U.S. Cl.
CPC ............ *E21B 47/003* (2020.05); *E21B 43/26* (2013.01); *G01N 33/241* (2013.01)

(58) Field of Classification Search
CPC ..... E21B 47/003; E21B 43/26; G01N 33/241; G01N 33/24
See application file for complete search history.

(56) References Cited

U.S. PATENT DOCUMENTS

| | | | |
|---|---|---|---|
| 9,874,551 B2 * | 1/2018 | Herron .................... | G01N 33/24 |
| 2009/0289628 A1 * | 11/2009 | Cao Minh ................ | G01V 3/32 |
| | | | 324/303 |
| 2016/0266274 A1 | 9/2016 | Alqam et al. | |

(Continued)

FOREIGN PATENT DOCUMENTS

| | | | | |
|---|---|---|---|---|
| CN | 105927218 | * | 5/2019 | ............ E21B 49/00 |
| CN | 109753302 | * | 5/2019 | |
| WO | WO-2016032489 A1 | * | 3/2016 | ......... E21B 41/0092 |

OTHER PUBLICATIONS

C. Naides "Petrophysical Analysis Method To Identify "Sweet Spots" in Tight Gas Reservoirs: Case Study From Punta Rosada Formation in Neuquen Basin Argentina" SPE 121313;Copuright 2010, Society of Petroleun engineers, pp. 1-16 (Year: 2010).*

(Continued)

*Primary Examiner* — Michael J Dalbo
*Assistant Examiner* — Kaleria Knox
(74) *Attorney, Agent, or Firm* — Fish & Richardson P.C.

(57) ABSTRACT

Systems and methods include a computer-implemented method: Total clay, effective porosity (PHIE) values, and gas volume are determined for a tight gas sandstone reservoir characterization using petrophysical evaluation results. Regions of the tight gas sandstone reservoir are characterized, including performing diagenetic rock typing for the regions using the total clay and PHIE values, where the diagenetic rock typing reflects porosity/permeability and clay content change. Sweet spots are determined based on the diagenetic rock typing and gas volume variation. Ranked sweet spots are determined by indexing and ranking the sweet spots by category. Optimized infill drilling locations and target zones are determined, and well placements in the tight gas sandstone reservoir are assisted using the diagenetic rock typing and the ranked sweet spots.

17 Claims, 17 Drawing Sheets

(56) References Cited

U.S. PATENT DOCUMENTS

| | | | |
|---|---|---|---|
| 2017/0260855 A1* | 9/2017 | Yang | E21B 49/005 |
| 2018/0003653 A1* | 1/2018 | Tinni | G01N 15/08 |
| 2018/0031732 A1 | 2/2018 | Mosse et al. | |
| 2019/0025461 A1* | 1/2019 | Wiener | G01V 99/005 |
| 2019/0055842 A1 | 2/2019 | Lu | |

OTHER PUBLICATIONS

Alexander C. Monsees, "Rock typing of diagenetically induced heterogeneities—A case study from a deeply-buried clastic Rotliegend reservoir of the Northern German Basin", pp. 1-14, Marine and Petroleun Geology, Research paper, Elsevier (Year: 2019).*

Cui et al., "Prediction of diagenetic facies using well logs—a case study from the upper Triassic Yanchang Formation, Ordos Basin, China," Marine and Petroleum Geology, 2017, 81:50-65.

De Segonzac et al., "The birth and development of the concept of diagenesis," Earth Science Reviews, 1968, 4:153-201.

Desbois et al., "High-resolution 3D fabric and porosity model in a tight gas sandstone reservoir: a new approach to investigate microstructures from mm-to nm-scale combing argon beam cross sectioning and SEM imaging," Journal of Petroleum Science and Engineering, 2011, 78:243-257.

Higgs et al., "Diagenesis, porosity evolution, and petroleum emplacement in tight gas reservoirs, Taranaki Basin, New Zealand," Journal Sedimentary Research, 2007, 77:1003-1025.

Lai et al., "Fractal analysis of tight shaly sandstones using nuclear magnetic resonance measurements," AAPG Bulletin, Feb. 2018, 102(2):175-193.

Liu et al., "Diagenetic facies controls on pore structure and rock electrical parameters in tight gas sandstone," Journal Geophysical Engineering, 2015, 12(4):587-600.

Schmid et al., "Diagenesis and reservoir quality of the Sherwood Sandstone (Triassic), Corrib Field, Slyne Basin, West of Ireland," Marine and Petroleum Geology, 2004, 21:299-315.

Monsees et al., "Rock typing of diagenetically induced heterogeneities—a case study from a deeply-buried clastic Rotliegend Reservoir of the Northern German Basin," Marine and Petroleum Geology, Dec. 2019, 113, 15 pages.

PCT International Search Report and Written Opinion in International Appln. No. PCT/US2021/053737, dated Feb. 1, 2022, 16 pages.

* cited by examiner

PPL FIELD VIEW APPROX. 1mm

1100

```
1   import numpy as np
2   from Techlog import MissingValue
3   def myVtotal(volillite,volkaolin,volchlor):
4   >>    if volillite == MissingValue:
5   >>       >>   volillite = 0
6   >>    if volkaolin == MissingValue:
7   >>       >>   volkaolin = 0
8   >>    if volchlor == MissingValue:
9   >>       >>   volchlor = 0
10  >>    return (volillite+volkaolin+volchlor)
11
12  LOOP:
13  >>    vol_total= myVtotal(volillite,volkaolin,volchlor)
14  >>    if volquartz >= 0.75:
15  >>       >>   qo=volquartz - 0.75
16  >>    else:
17  >>       >>   qo=0
18  >>    if phie == MissingValue:
19  >>       >>   drt == MissingValue
20  >>    elif phie >= PHIE_CUTOFF1:
21  >>       >>   if vol_total < VOL_CUTOFF1:
22  >>       >>      >>   drt = 6
23  >>       >>   elif vol_total >= VOL_CUTOFF1:
24  >>       >>      >>   drt = 5
25  >>    elif phie > PHIE_CUTOFF2 and phie < PHIE_CUTOFF1:
26  >>       >>   if vol_total < VOL_CUTOFF2:
27  >>       >>      >>   drt = 4
28  >>       >>   elif vol_total >= VOL_CUTOFF2:
29  >>       >>      >>   drt = 3
30  >>    elif phie <= PHIE_CUTOFF2:
31  >>       >>   if vol_total < VOL_CUTOFF3:
32  >>       >>      >>   drt = 2
33  >>       >>   elif vol_total >= VOL_CUTOFF3:
34  >>       >>      >>   drt = 1
35  >>    else:
36  >>       >>   drt == MissingValue
37  >>
38  >>    if vol_total == MissingValue:
39  >>       >>   fi = MissingValue
40  >>    else:
41  >>       >>   fi = phie/(vol_total+0.1)
```

FIG. 11A

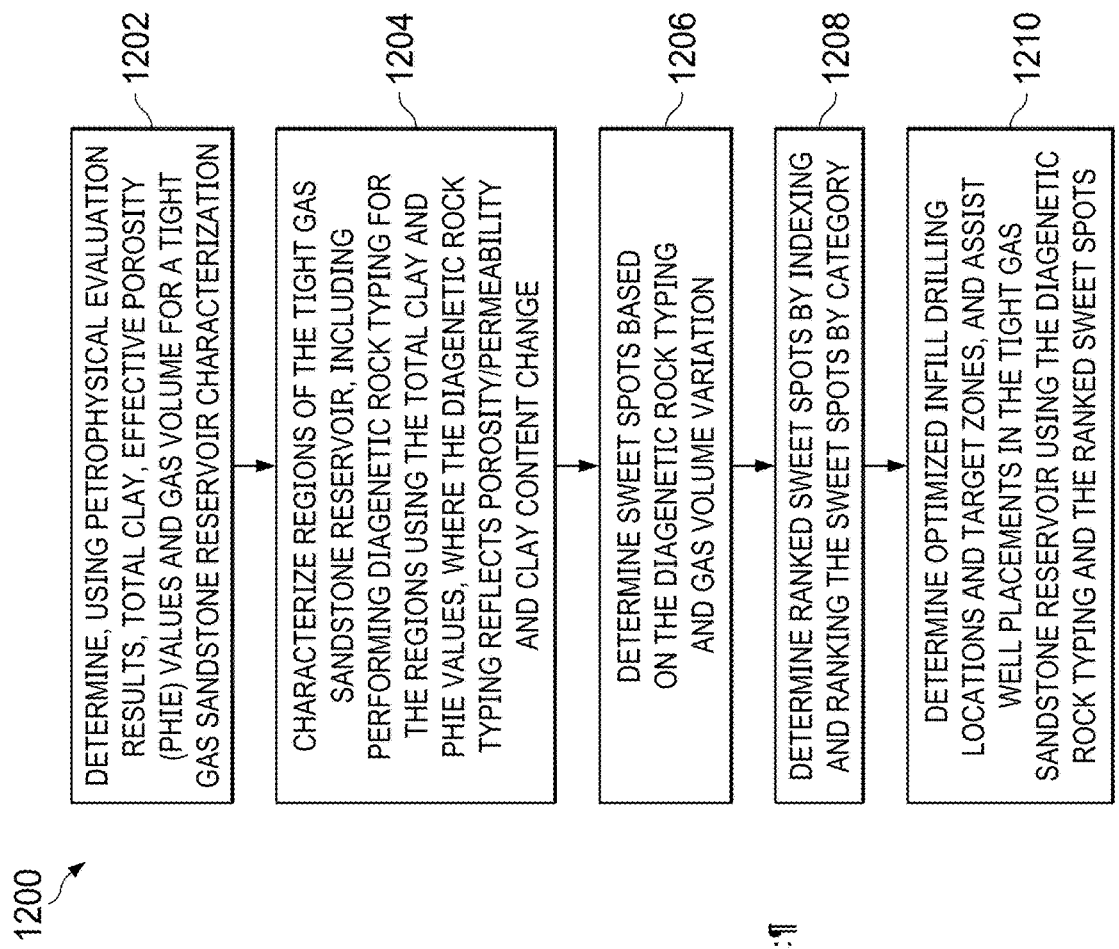

… (1 / 11) …

LOG BASED DIAGENETIC ROCK TYPING AND SWEET SPOT IDENTIFICATION FOR TIGHT GAS SANDSTONE RESERVOIRS

BACKGROUND

The present disclosure relates to tight gas sandstone reservoir characterization.

Tight sandstone reservoirs have become more important over time because of their vast distribution and hydrocarbon accumulation. Tight sandstones can be characterized by low porosity/permeability due to heavy compaction and various diagenetic minerals cementation over geological time. Reservoir quality, especially porosity/permeability, can be a reflection of initial sediment composition and subsequent diagenetic modifications.

Diagenesis refers to the physical and chemical process that occurs from the start of deposition, continuing through compaction, cementation, and dissolution. Diagenetic alterations can have a strong impact on reservoir quality and heterogeneity of tight sandstone. Previous studies have shown that the reservoir quality of sandstone is related to burial depth, sandstone composition and texture, and authigenic cements.

Diagenetic facies, defined as the combination of types and degree of diagenesis and diagenetic minerals, can be defined using a set of wireline logs. Prediction of diagenetic facies in sandstone by conventional wireline logs has been widely used and studied. Reservoir quality prediction for un-cored intervals or un-cored wells can also be made.

The efficient exploration and development of tight sandstone reservoirs in a given geological setting can largely depend on the level of understanding of the impact of diagenetic alteration on the sandstone reservoir quality. A "sweet spot" identification can be useful for field development in terms of well location and target zones for horizontal drilling.

SUMMARY

The present disclosure describes techniques that can be used for determining optimized infill locations, target zones for well placements in tight gas sandstone reservoirs using diagenetic rock typing and ranked sweet spots. In some implementations, a computer-implemented method includes the following. Total clay, effective porosity (PHIE) values, and gas volume are determined for a tight gas sandstone reservoir characterization using petrophysical evaluation results. Regions of the tight gas sandstone reservoir are characterized, including performing diagenetic rock typing for the regions using the total clay and PHIE values, where the diagenetic rock typing reflects porosity/permeability and clay content change. Sweet spots are determined based on the diagenetic rock typing and gas volume variation. Ranked sweet spots are determined by indexing and ranking the sweet spots by category. Optimized infill drilling locations and target zones are determined, and well placements in the tight gas sandstone reservoir are assisted using the diagenetic rock typing and the ranked sweet spots.

The techniques of the present disclosure can use petrophysical evaluation results as an input. The results of three-dimensional (3D) tight sandstone reservoir characterization can be improved by using greater amounts of well data. The techniques of the present disclosure can be applied to single wells and multiple wells.

The previously described implementation is implementable using a computer-implemented method; a non-transitory, computer-readable medium storing computer-readable instructions to perform the computer-implemented method; and a computer-implemented system including a computer memory interoperably coupled with a hardware processor configured to perform the computer-implemented method/the instructions stored on the non-transitory, computer-readable medium.

The subject matter described in this specification can be implemented in particular implementations, so as to realize one or more of the following advantages. First, the techniques of the present disclosure can help to solve the problem of reservoir heterogeneity characterization for tight gas sandstone reservoirs in terms of integration of porosity, clay contents, gas volume, and frackability, and eventually to identify sweet spots. Second, log-based diagenetic rock typing can be accomplished by using existing petrophysical evaluation results. Third, sweet spot computations and sweet spot determinations can be based on diagenetic rock type and gas volume. Fourth, the techniques of the present disclosure can be applied to a real sandstone reservoir diagenetic rock typing and sweet spot mapping project. The results can be verified using production data (for example, using flow back rates). Fifth, the techniques of the present disclosure can be more effective and efficient for locating sweet spots for infill drilling. This can be especially useful for considering rock frackability, and can serve as a main component for tight gas reservoir characterization. Conventional techniques, such as limited to depositional facies, reservoir porosity, permeability, and gas/water saturation modeling used for reservoir characterization, may have limitations in terms of sweet spot identification. For example, depositional facies typically do not reflect porosity/permeability changes, and better porosity/permeability sandstone may have lower gas saturations. Sixth, the sweet spots that are located using techniques of the present disclosure can be combined with diagenetic rock type (reflecting porosity/clay content changes), gas volume variation, and rock frackability. This can provide improvements over conventional reservoir characterization methods. Seventh, petrochemical (for example, oil and gas) companies can use the techniques to conduct field studies to characterize similar tight gas sandstone reservoirs.

The details of one or more implementations of the subject matter of this specification are set forth in the Detailed Description, the accompanying drawings, and the claims. Other features, aspects, and advantages of the subject matter will become apparent from the Detailed Description, the claims, and the accompanying drawings.

DESCRIPTION OF DRAWINGS

FIG. 11A is an example of a script that was programmed to assist the diagenetic rock typing processing, according to some implementations of the present disclosure.

FIG. 11B is an example of a script that was programmed to assist the 1D sweet spot index computation and flag process, according to some implementations of the present disclosure.

FIG. 12 is a flowchart of an example of a method for determining optimized infill locations, target zones, and well placements in a tight gas sandstone reservoir using diagenetic rock typing and ranked sweet spots, according to some implementations of the present disclosure.

Like reference numbers and designations in the various drawings indicate like elements.

DETAILED DESCRIPTION

Figure 1:
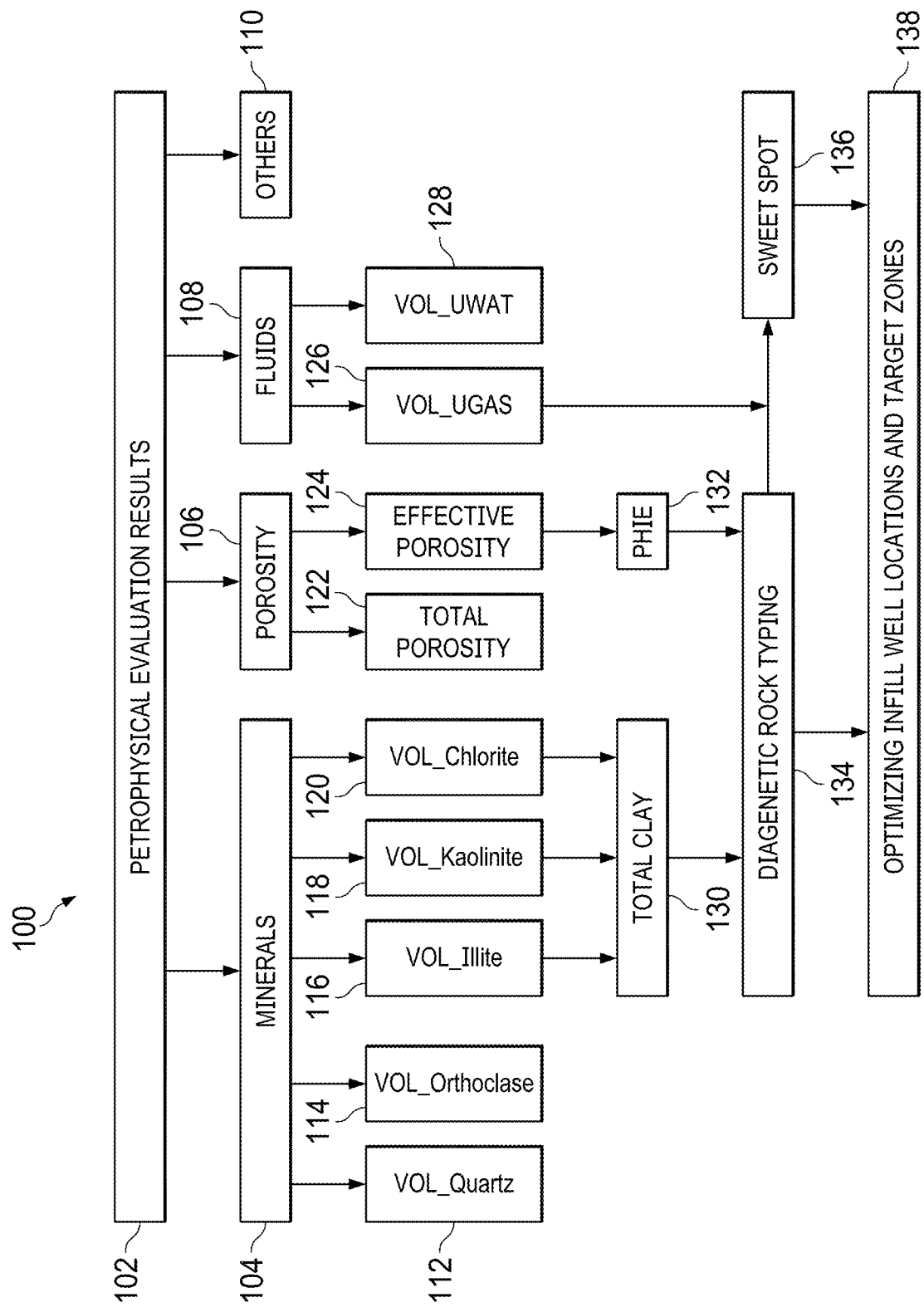
FIG. 1 is a block diagram showing an example of a process for optimizing infill well locations and target zones, according to some implementations of the present disclosure.

The following detailed description describes techniques for determining optimized infill drilling locations, target zones for well placements in tight gas sandstone reservoirs using diagenetic rock typing and ranked sweet spots. A tight gas sandstone reservoir can be defined, for example, as having less than 0.1 millidarcy (mD) matrix permeability and less than 10% matrix porosity. A sweet spot can be defined, for example, as having a computed SSP (sweet spot) index curve greater than 1 in a one-dimensional (1D) domain that can produce gas after hydraulic fracking, and/or an area that has a higher thickness or percentage of good and moderate gas-bearing sands.

Various modifications, alterations, and permutations of the disclosed implementations can be made and will be readily apparent to those of ordinary skill in the art, and the general principles defined may be applied to other implementations and applications, without departing from scope of the disclosure. In some instances, details unnecessary to obtain an understanding of the described subject matter may be omitted so as to not obscure one or more described implementations with unnecessary detail and inasmuch as such details are within the skill of one of ordinary skill in the art. The present disclosure is not intended to be limited to the described or illustrated implementations, but to be accorded the widest scope consistent with the described principles and features.

The techniques of the present disclosure can directly use existing petrophysical evaluation results to perform diagenetic rock typing and sweet spot identification, for example, combining porosity, clay content, gas volume, and frackability to evaluate the sweet spots. Diagenetic rock typing can be performed first based on the effective porosity and total clay content, and the results can be combined with the gas volume to generate a sweet spot index curve. For example, the sweet spot index curve can be composed of three categories (for example, good, moderate, and poor), considering the gas volume and sandstone frackability. The results can greatly help to optimize well location selection for infill drilling, target zone selection for well placement, and interval selection for hydraulic fracking. Diagenetic rock typing is a primary component of the techniques of the present disclosure, using existing petrophysical evaluation results, petrography study results, and under balanced coil tubing drilling results as the diagenetic rock typing criteria.

Strong heterogeneities, such as porosity/permeability, clay type and content may be observed in deep buried tight sandstone gas reservoirs due to a long geological history of extensive diagenetic processes. Traditional methods for characterizing these kinds of gas reservoirs can be challenging, since fracking is needed in most of the cases. As a result, the quality of these kinds of tight sandstone reservoir not only relies on the porosity/permeability and clay content, but also on the frackability.

A petrophysical log-based diagenetic rock typing and sweet spot identification process can provide a more effective and efficient process for characterizing tight sandstone reservoirs in terms of reservoir heterogeneity, and for locating sweet spots. The results can greatly help to optimize well location selection for infill drilling, target zone selection for well placement, and interval selection for hydraulic fracking.

Sandstone petrography studies have shown that sandstone mainly consists of quartz and minor feldspars as grain contents, cements including quartz overgrowth, illite, kaolinite, and chlorite. The studies have provided a solid foundation for wireline log-based petrophysical evaluation in terms of a mineralogy model setup.

A main feature of the present disclosure includes diagenetic rock typing, which uses existing petrophysical evaluation results to generate different diagenetic rock types according to effective porosity and total clay content variations (FIG. 1). Compaction and cementation are two main diagenetic processes for reducing sandstone intergranular porosity and permeability, producing a tight sandstone.

Compaction is usually a function of burial depth, and heavy compaction is expected with increased burial depth. Cementation may be a greater contributor to the diagenetic process than compaction for the same sandstone reservoir since heterogeneity is mainly caused by different types and amounts of the cement. For example, quartz cemented clean sandstone has much better porosity and permeability than clay rich sandstones, especially permeability in case of similar porosity. Therefore, the clay content, including illite, kaolinite, and chlorite is critical for different diagenetic rock types. That is why total clay is used in the present disclosure as one of the key factors to perform sandstone diagenetic rock typing.

FIG. 1 is a block diagram showing an example of a process 100 for optimizing infill well locations and target zones, according to some implementations of the present disclosure. The process 100 uses sandstone petrophysical evaluation results 102, including minerals 104, porosity 106, fluids 108, and others 110 (for example, including water saturation (Sw), permeability (Perm). The results can include quartz volume (vol) 112, orthoclase volume 114, illite volume 116, kaolinite volume 118, chlorite volume 120, total porosity 122, effective porosity 124, gas volume (VOL_UGAS) 126, and water volume (VOL_UWAT) 128. Outputs of the process 100 include total clay 130 and effective porosity (PHIE) 132, from which diagenetic rock typing 134 can identified. Consequently, diagenetic rock typing results can be integrated with VOL_UGAS 126 to identify sweet spots 136. The output of process 100 includes optimizing infill well locations and target zones 138.

Diagenetic rock typing criteria are based on sandstone petrography studies, for example, in which the total clay content is less than 5% in clean sandstones. In under balanced coil tubing drilling (UBCTD) results, for example, clean sandstone with a 5% porosity can naturally produce gas. Sandstone frackability analysis results, for example, can determine that sandstone has more than 3% porosity and less than 10% total clay. Considering all the above mentioned factors, tight sandstone can be divided, for example, into six different types of diagenetic rock types (DRT), namely Types 1-6 (Table 1).

Table 1 lists examples of diagenetic rock typing criteria for tight sandstone, including PHIE and total clay:

TABLE 1

Diagenetic Rock Typing Criteria

| Diagenetic Rock Type | Code | PHIE | Total Clay |
| --- | --- | --- | --- |
| Type 1 | 6 | PHIE ≥ 5% | <5% |
| Type 2 | 5 | PHIE ≥ 5% | ≥5% |
| Type 3 | 4 | 3% ≤ PHIE < 5% | <10% |
| Type 4 | 3 | 3% ≤ PHIE < 5% | ≥10% |
| Type 5 | 2 | <3% | <20% |
| Type 6 | 1 | <3% | ≥20% |

Figure 2:
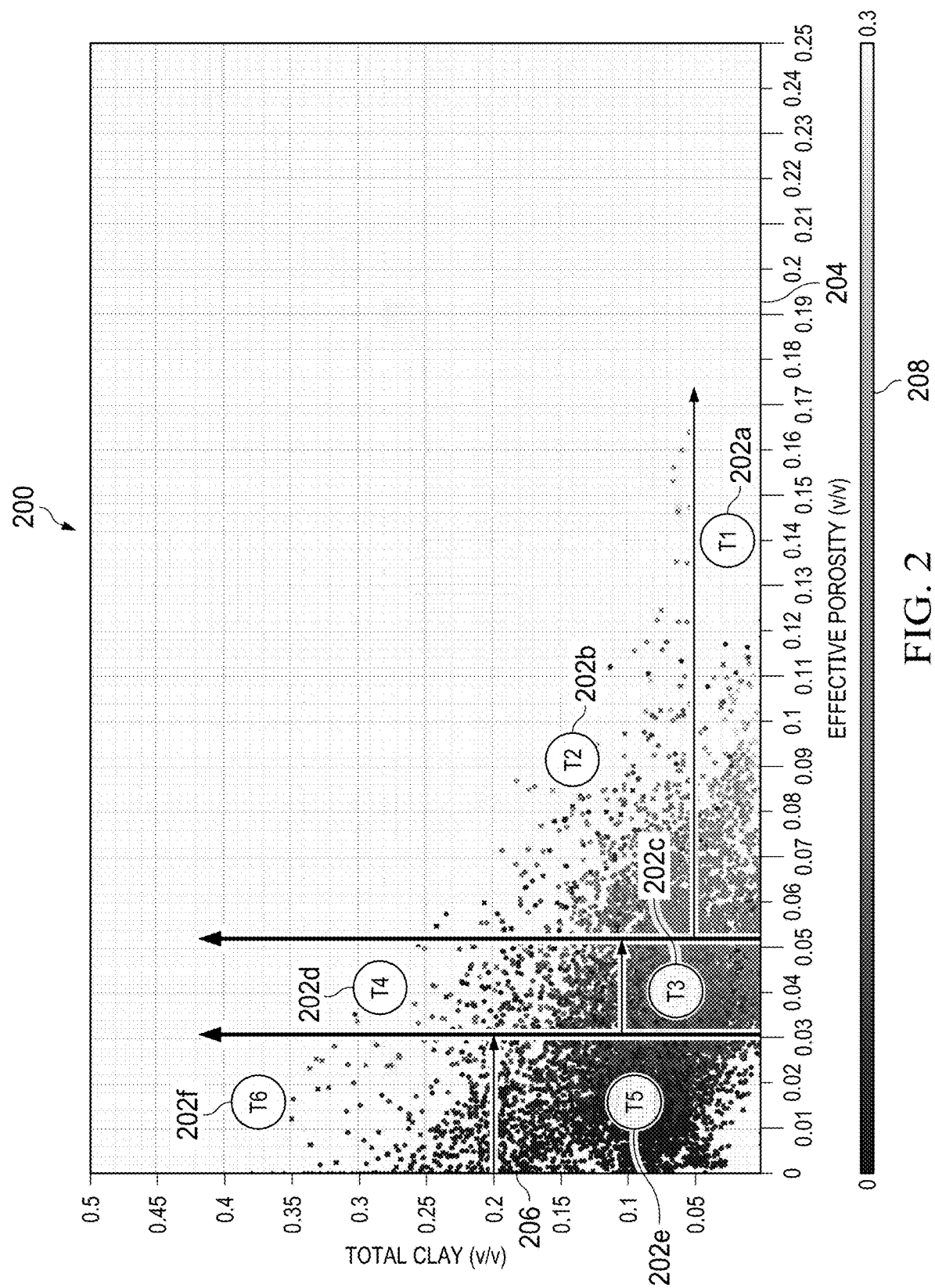
FIG. 2 is a cross plot showing examples of types of diagenetic rock, according to some implementations of the present disclosure.

FIG. 2 is a cross plot 200 showing examples of types of diagenetic rock, according to some implementations of the present disclosure. FIG. 2 shows tight sandstone PHIE versus total clay cross plot, and color change reflect VOL_UGAS variation in the tight sunstone, for example. The studied tight sandstone can be divided into six different diagenetic rock types 1-6, based on their effective porosity and total clay variations. The numbers in regions of 202a-202f in the cross plot of FIG. 2 correspond to the different diagenetic rock types in Table 1. A python script (FIG. 11A) was programmed to assist the diagenetic rock typing processing, which can be applied for either single well or multiple wells. The cross plot of FIG. 2 includes an x-axis 204 of effective porosity (for example, in decimal units (v/v)), a y-axis 206 of total clay (for example, in decimal units) and gas volume 208 (for example, in decimal units and shades of gray).

Figure 3:
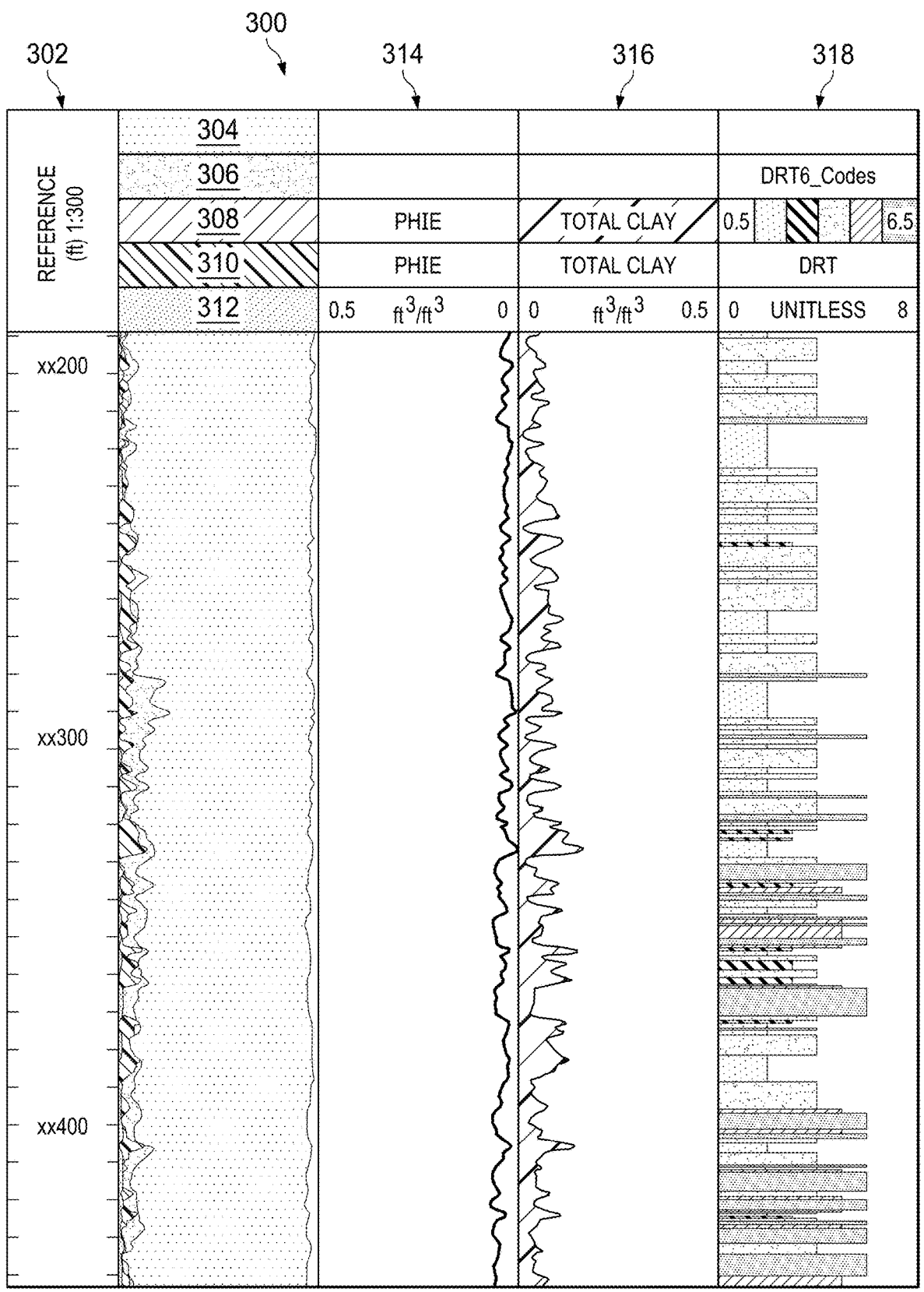
FIG. 3 is a plot showing example results of tight sandstone diagenetic rock typing, according to some implementations of the present disclosure.

FIG. 3 is a plot 300 showing example results of tight sandstone diagenetic rock typing, according to some implementations of the present disclosure. The lower part of the plot 300 shows much better diagenetic rock type than the upper part of the plot 300. The plot 300 is plotted relative to a depth 302 (for example, in feet (ft)). Volume (petrophysical evaluation mineralogy) percentages include a quartz volume 304, an orthoclase (ORTHOCL) volume 306, a kaolinite volume 308, an illite volume 310, and a chlorite volume 312. Many layers show higher effective porosity (PHIE) 314 (for example, in cubic feet per cubic feet ($ft^3/ft^3$)) and lower total clay content 316, which is the lump sum of kaolinite volume 308, illite volume 310, and chlorite volume 312. Studies have shown that good rock types are not necessary to have sweet spots (layers), such as, layers with higher water saturation (Sw) or lower gas volume (UGAS). Therefore, there is a need to combine these two together to generate a 1D sweet spot index and sweet spot flag. The plot 300 includes a diagenetic rock type (DRT) scale 318.

Sweet spots for tight gas reservoirs can refer to those sandstones with relatively higher gas volumes. Extraction of gas can occur either naturally, for example, porous gas bearing clean sandstone (Type 1), or after hydraulic fracking, for example those sands with lower porosity and higher clay content sands (Types 2 and 3). In some implementations, the 1D sweet spot index (SSP) can be expressed as:

$$SSP = DRT^3 \cdot UGAS \quad (1)$$

A python script (FIG. 11B) was programmed to assist the one-dimensional (1D) sweet spot index computation and flag process, which can be applied for either single well or multiple wells. The computed SSP curve can be further flagged into three categories: good (SSP>3), moderate (1<=SSP=<3), and poor (SSP<1), considering the gas volume and sandstone frackability.

Figure 4:
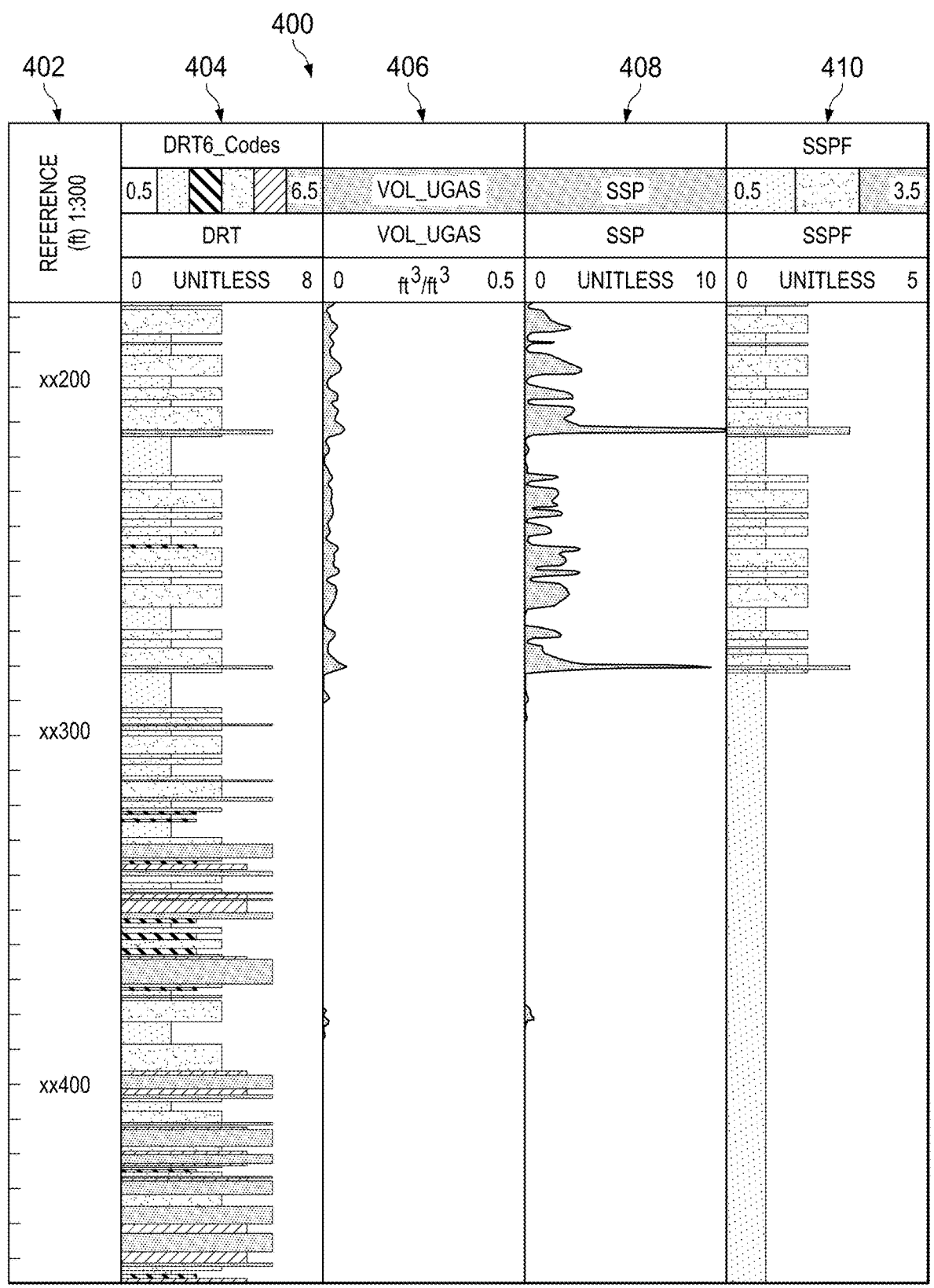
FIG. 4 is a plot showing an example of sandstone sweet spot one-dimensional (1D) index computation and flag results, according to some implementations of the present disclosure.

FIG. 4 is a plot 400 showing an example of sandstone sweet spot 1D index computation and flag results, according to some implementations of the present disclosure. The plot includes a depth 402, a diagenetic rock type 404, a gas volume (UGAS) 406, a computed sweet spot index curve (SSP) 408, and a sweet spot flag block curve 410 (SSPF: good, moderate and poor). The lower part of the plot 400 shows much better diagenetic rock type than the upper part of the plot 400, but the lower part is very poor in terms of sweet spots due to the very low gas volumes (high Sw). Some moderate reservoir sands were developed in the upper part of the well that was studied.

Both well log based diagenetic rock typing and sweet spot analysis results can be imported to any geological modeling software for 3D modeling. The advantage of facies or rock type modeling is that the results can be extracted as thickness and percentages for each individual rock type and sweet spot category or merged ones. This can help a geologist to identify sweet spot areas for infill drilling (FIGS. 5, 6, 7, and 8).

Studies have shown that the merged good and moderate sweet spot percentage map has very good agreement as compared to the flow back rate. A circle's size in FIG. 8 reflects the gas flow back rate, where a larger size of the circle indicates a higher flow back rate. Warm color areas (indicated by darker shades of gray) show higher flow back rates due to better diagenetic rock type and higher content of gas volume. Therefore, the warm color areas should be selected for future infill drilling. The present disclosure can be easily adapted for similar kinds of tight sandstone reservoir studies, especially useful for matured field development with abundant existing well data.

Figure 5:
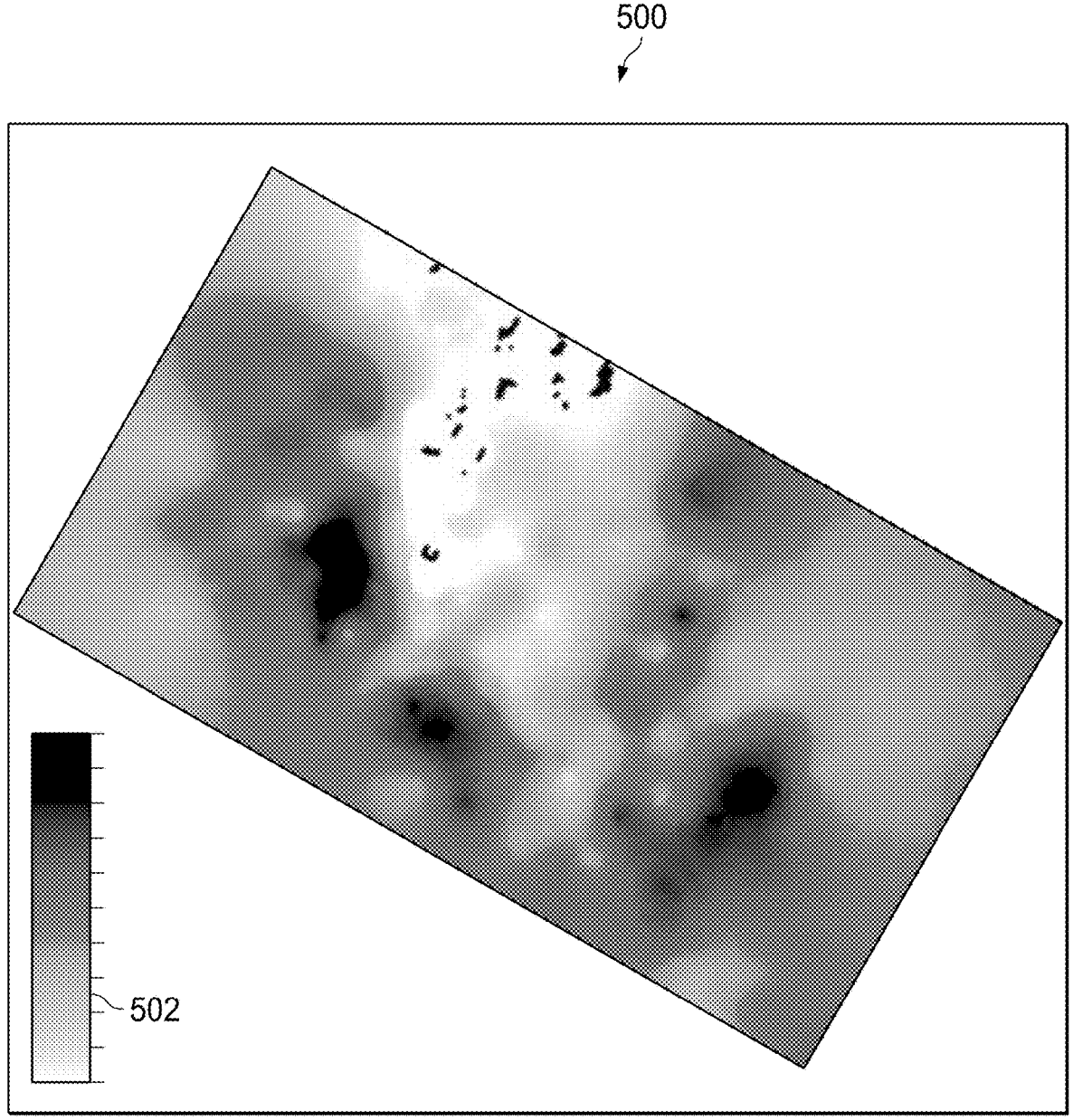
FIG. 5 is a map showing examples of merged Type 1, Type 2, and Type 3 diagenetic rock types' thickness varia

FIG. 5 is a map 500 showing examples of merged Type 1, Type 2, and Type 3 diagenetic rock types' thickness variations across a study area, according to some implementations of the present disclosure. In FIG. 5, according to a scale 502, a warm color (or darker shade of gray) area has thicker accumulative good reservoirs.

Figure 6:
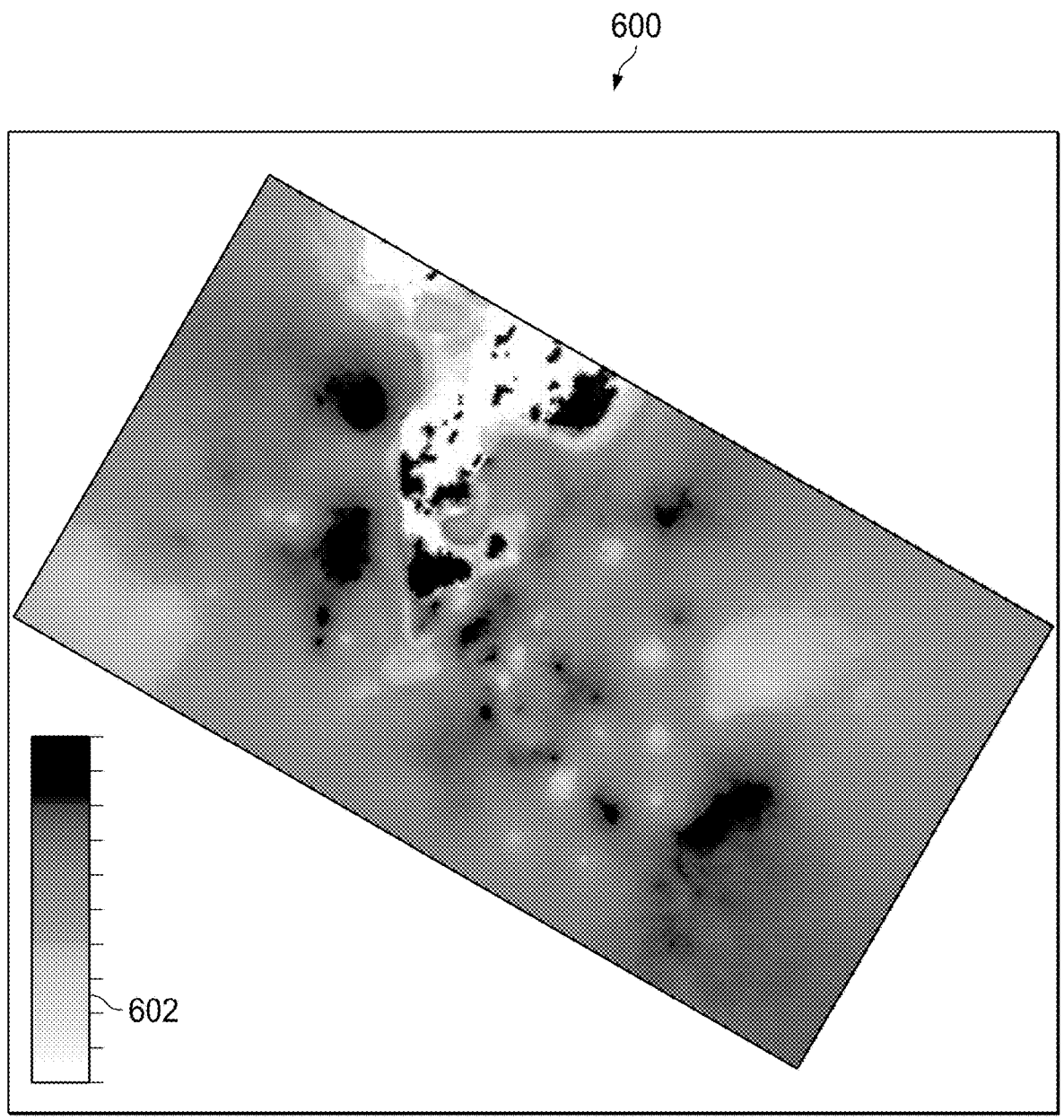
- FIG. 6 is a map showing examples of merged Type 1, Type 2, and Type 3 diagenetic rock types' percentage variations across a study area, according to some implementations of the present disclosure.

FIG. 6 is a map 600 showing examples of merged Type 1, Type 2, and Type 3 diagenetic rock types' percentage variations across a study area, according to some implementations of the present disclosure. In FIG. 6, according to a scale 602, a warm color (or darker shade of gray) area has higher percentage of good reservoir rock types.

Figure 7:
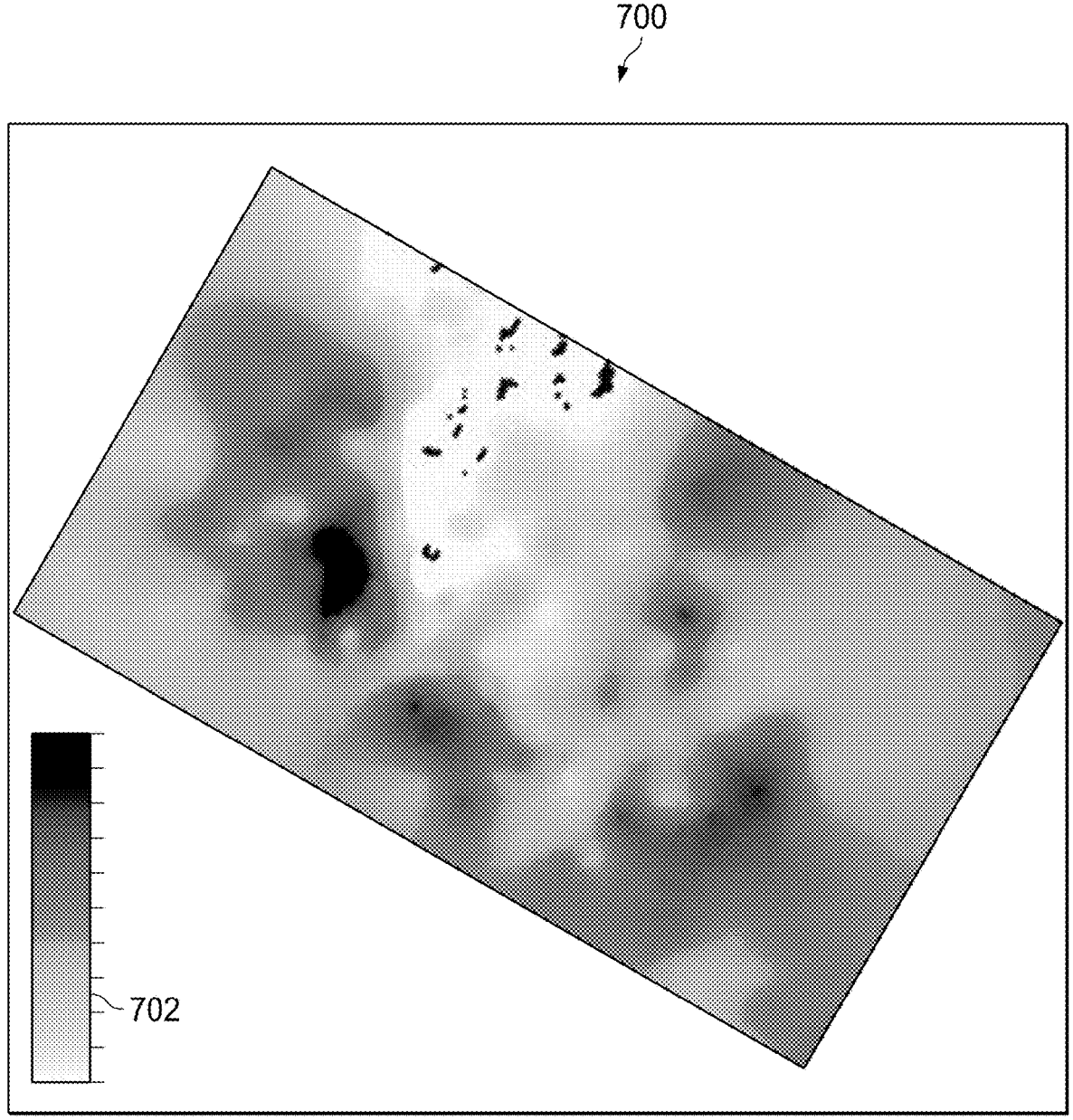
FIG. 7 is a map showing examples of merged good and moderate sandstone reservoir thickness variations across the study area, according to some implementations of the present disclosure.

FIG. 7 is a map 700 showing examples of merged good and moderate sandstone reservoir thickness variations across the study area, according to some implementations of the present disclosure. In FIG. 7, according to a scale 702, a warm color (or darker shade of gray) area has thicker accumulative good reservoirs.

Figure 8:
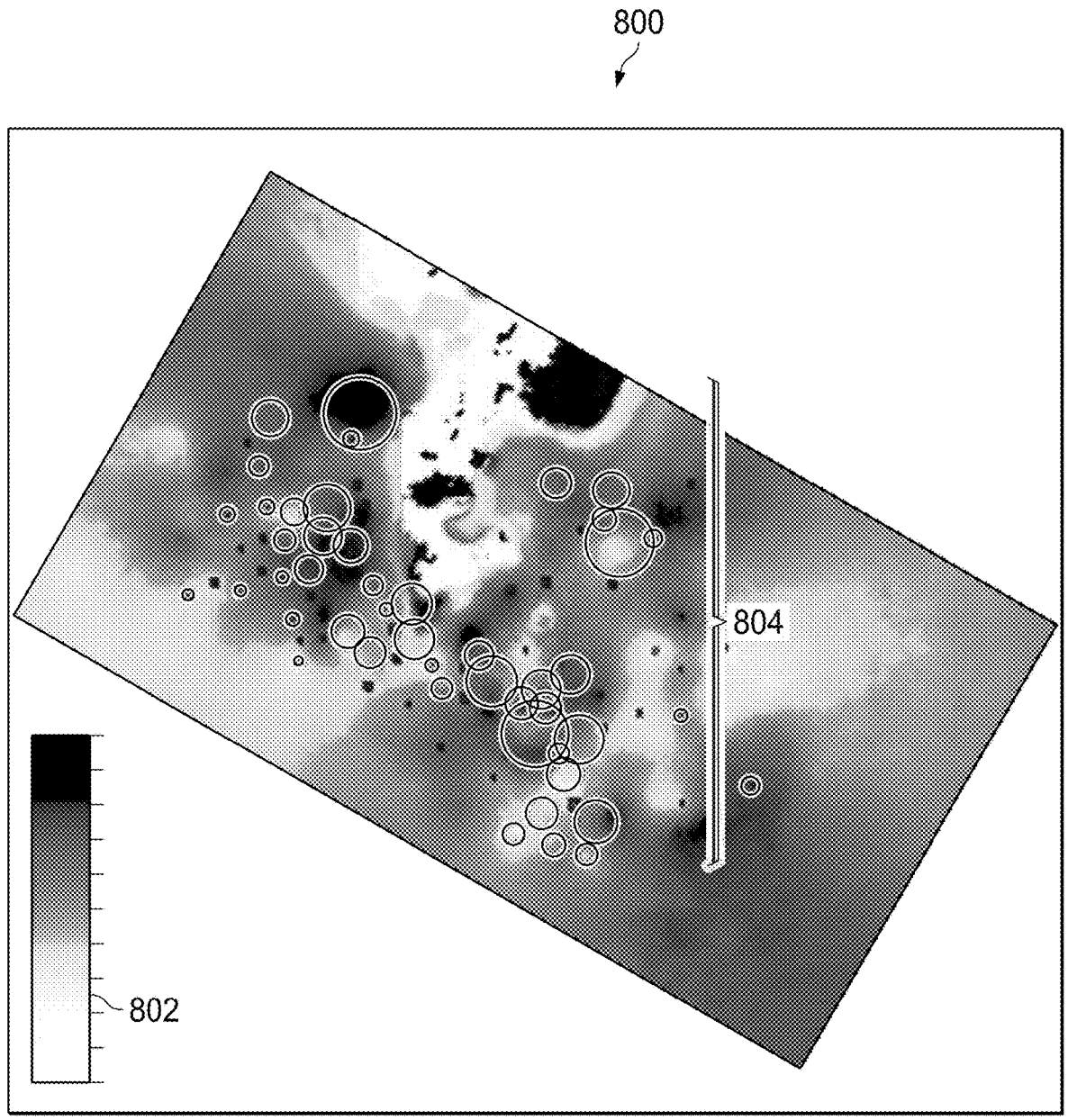
FIG. 8 is a map showing examples of merged good and moderate sandstone reservoir percentage variations across the study area, according to some implementations of the present disclosure.

FIG. 8 is a map 800 showing examples of merged good and moderate sandstone reservoir percentage variations across the study area, according to some implementations of the present disclosure. In FIG. 8, according to a scale 802, warm color (or darker shade of gray) areas have higher percentage of good reservoirs. Circles 804 indicate gas flow back rates (a larger size of a circle indicates a higher flow back rate).

Sandstone petrography studies have shown that sandstone mainly consists of quartz and minor feldspars as grain contents, cements including quartz overgrowth 902, illite 906, kaolinite, and chlorite (FIGS. 9 and 10). The studies have provided a solid foundation for wireline log-based petrophysical evaluation in terms of the mineralogy model setup. Compaction and cementation are two main diagenetic processes which reduce sandstone intergranular porosity and permeability, and make it become tight sandstone.

Figure 9A:
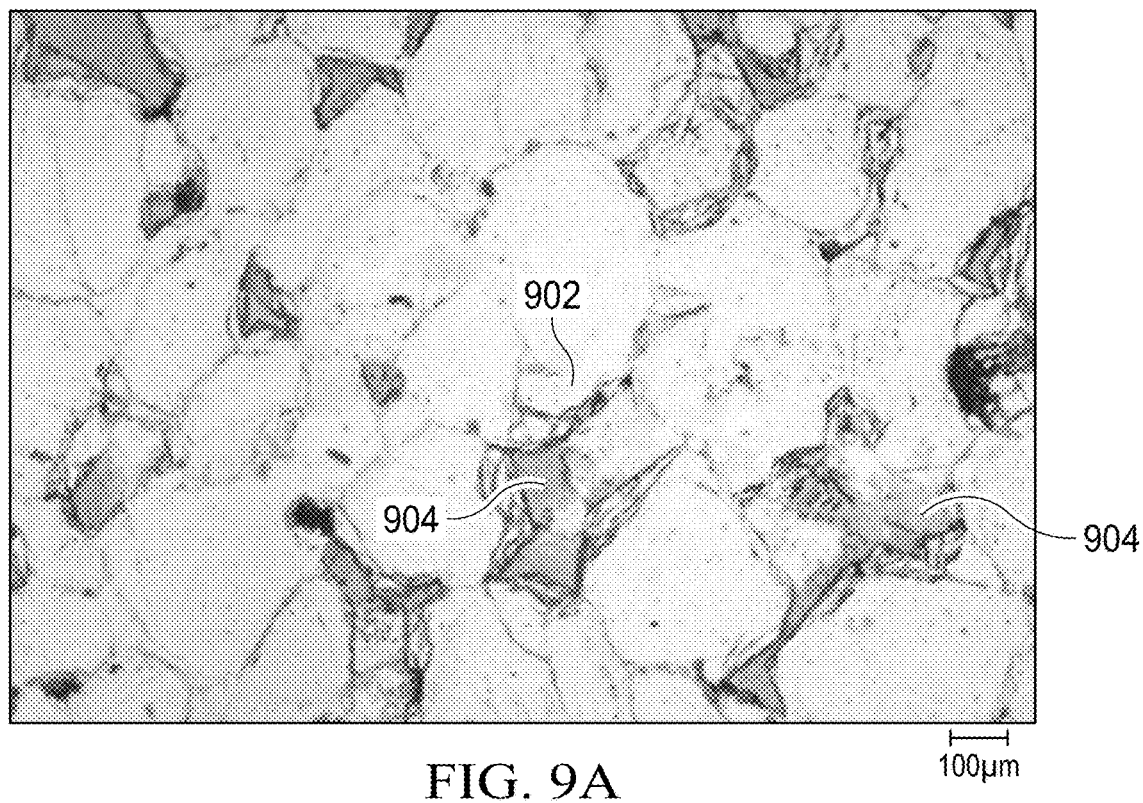
FIGS. 9A-9F show examples of plane polarized light thin section photos showing tight sandstone textures and their main components including framework grains and authigenic cements, according to some implementations of the present disclosure.
Figure 9B:
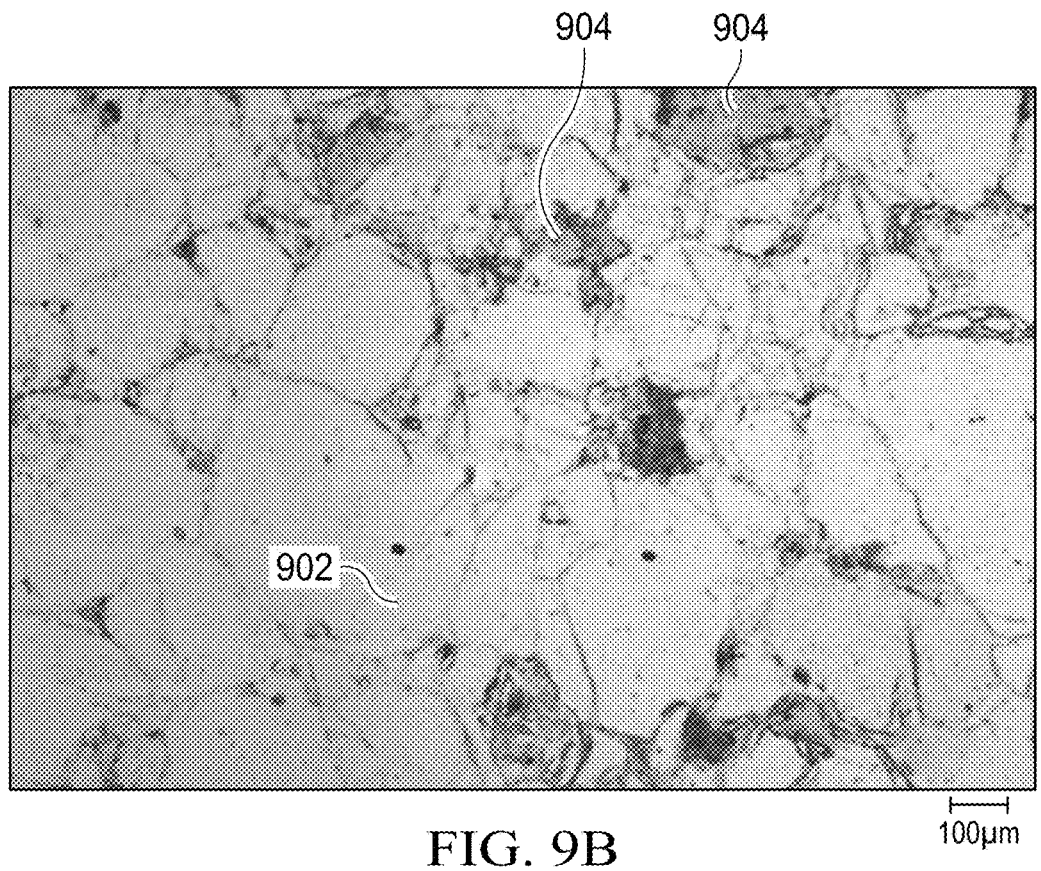
Figure 9C:
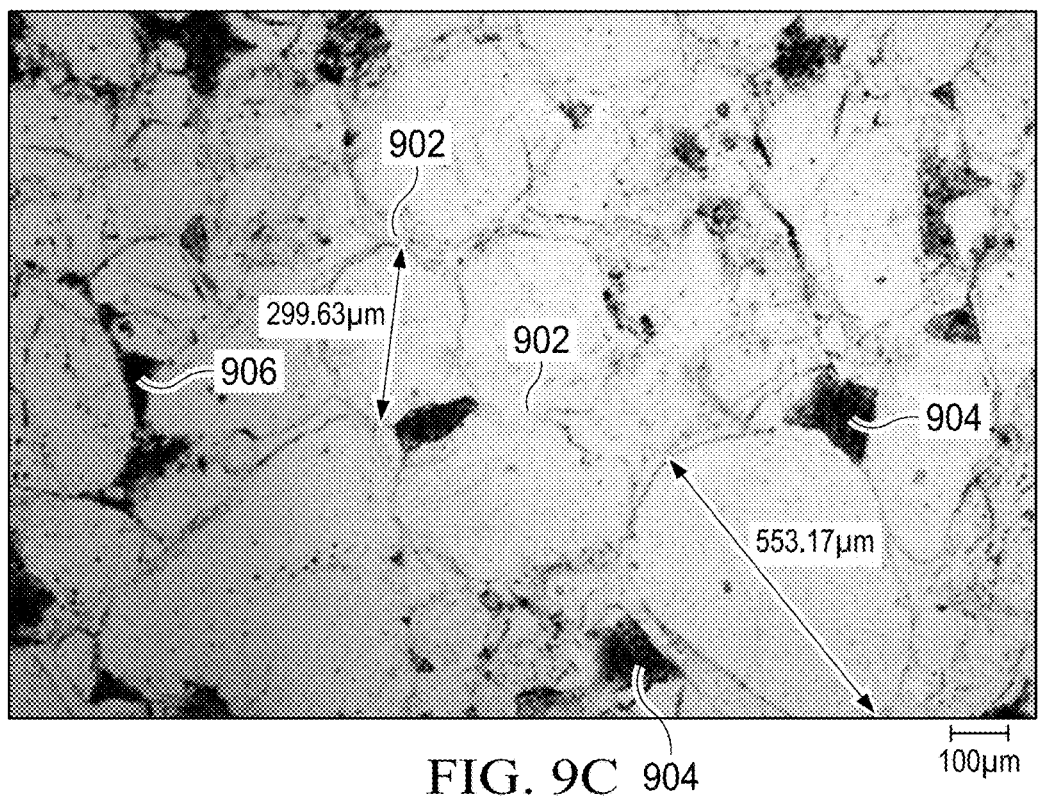
Figure 9D:
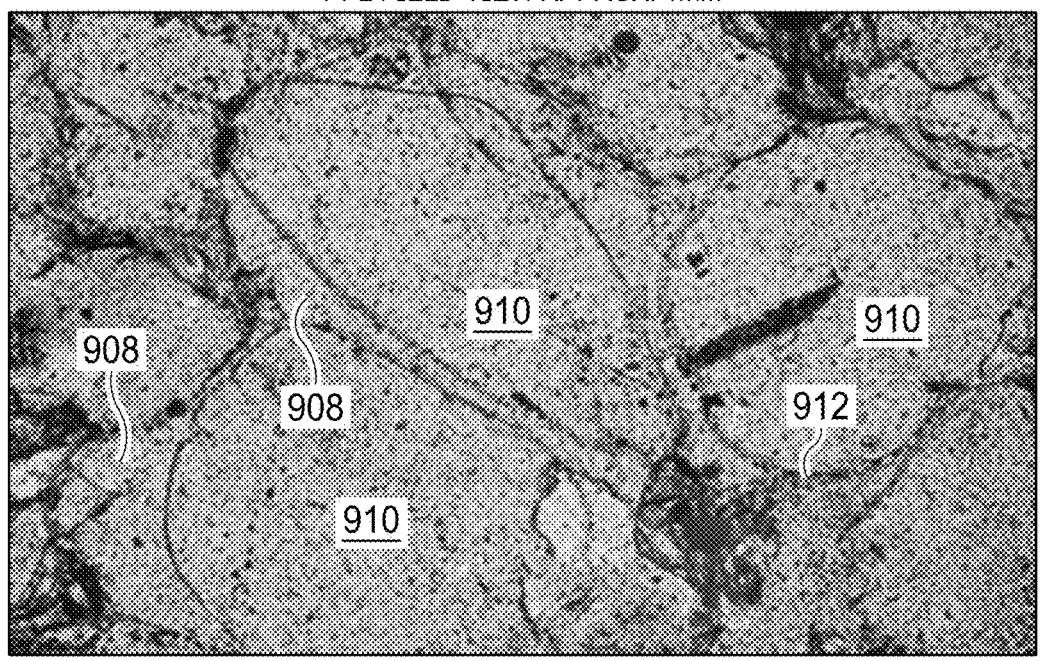
Figure 9E:
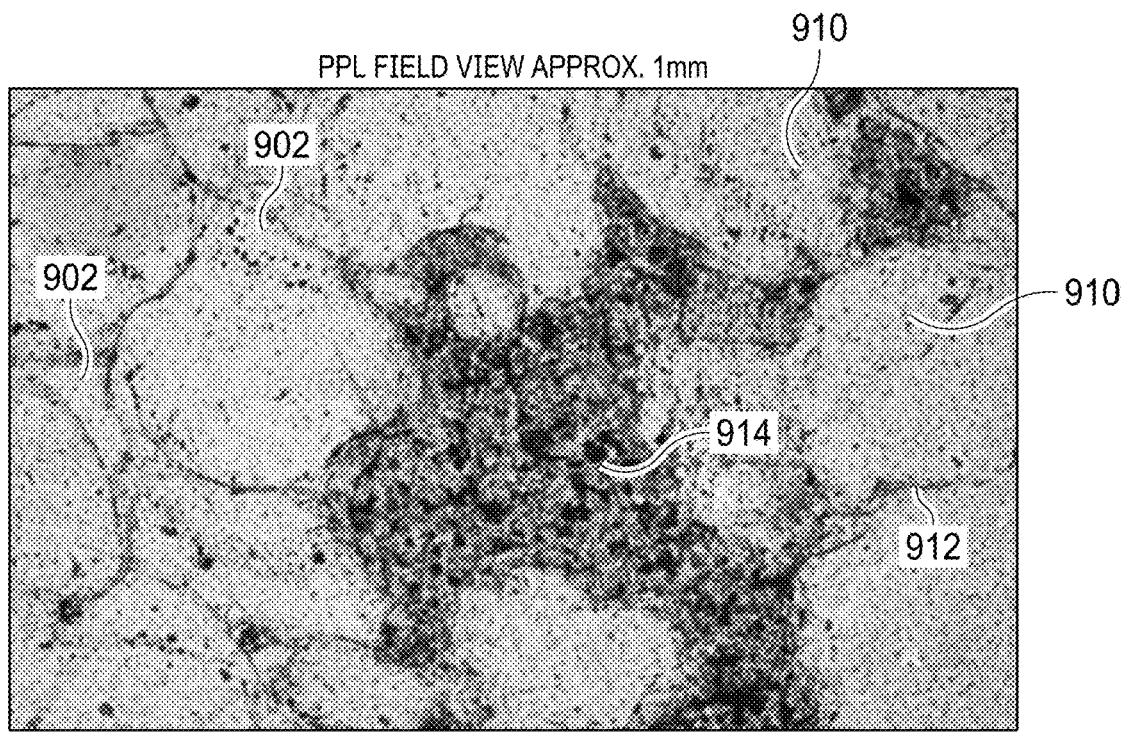
Figure 9F:
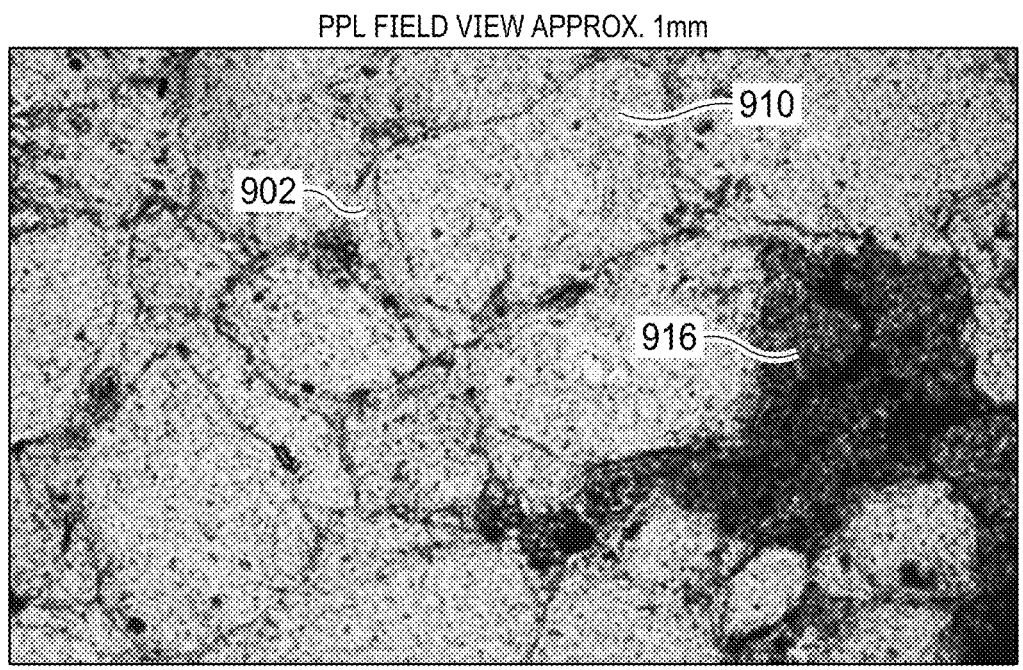
Figure 10A:
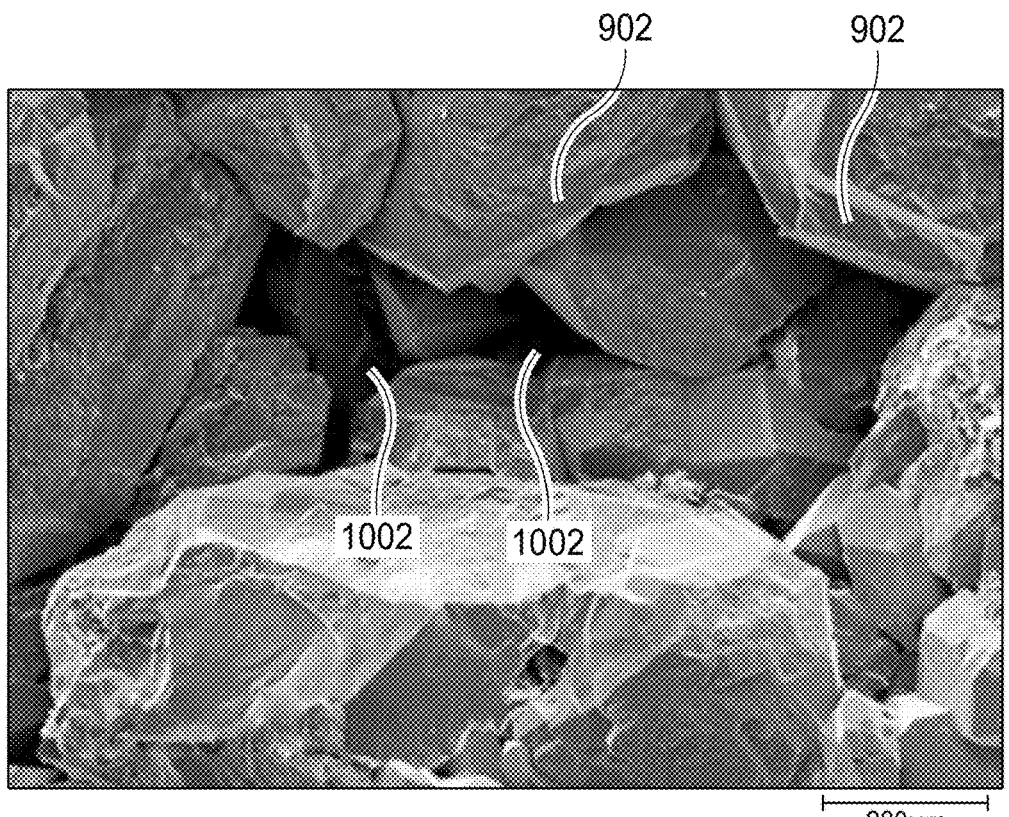
FIGS. 10A-10F show examples of scanning electric microscope (SEM) images showing tight sandstone three-dimensional (3D) textures and their main components including framework grains (quartz) and authigenic minerals, according to some implementations of the present disclosure.
Figure 10B:
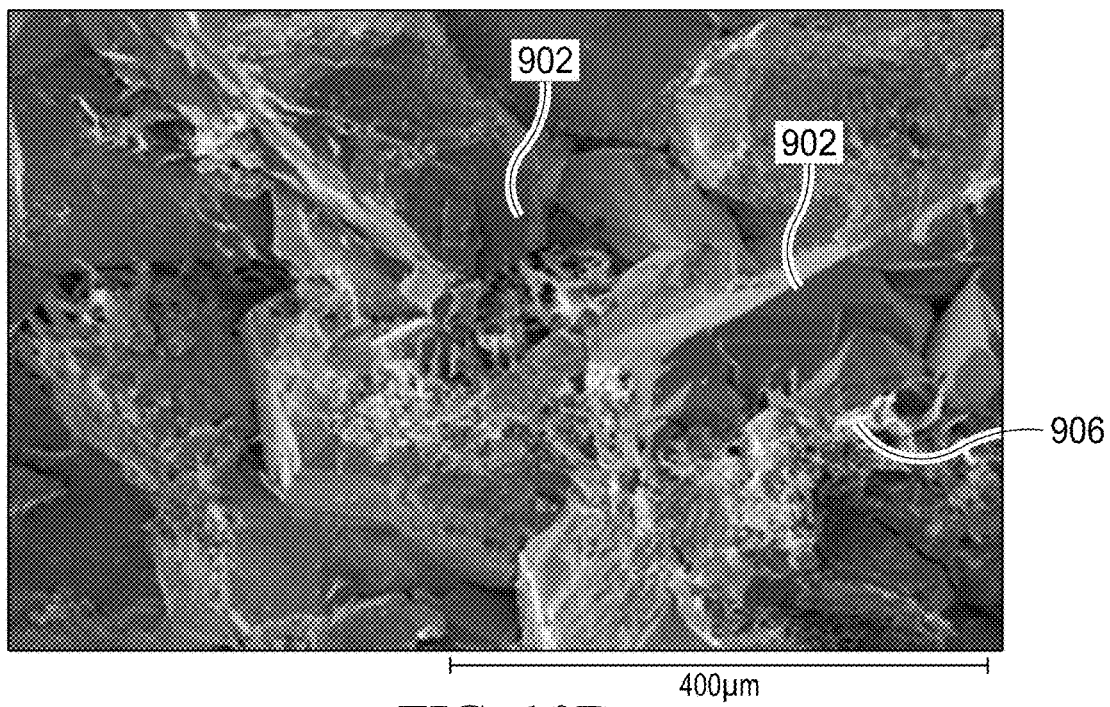
Figure 10C:
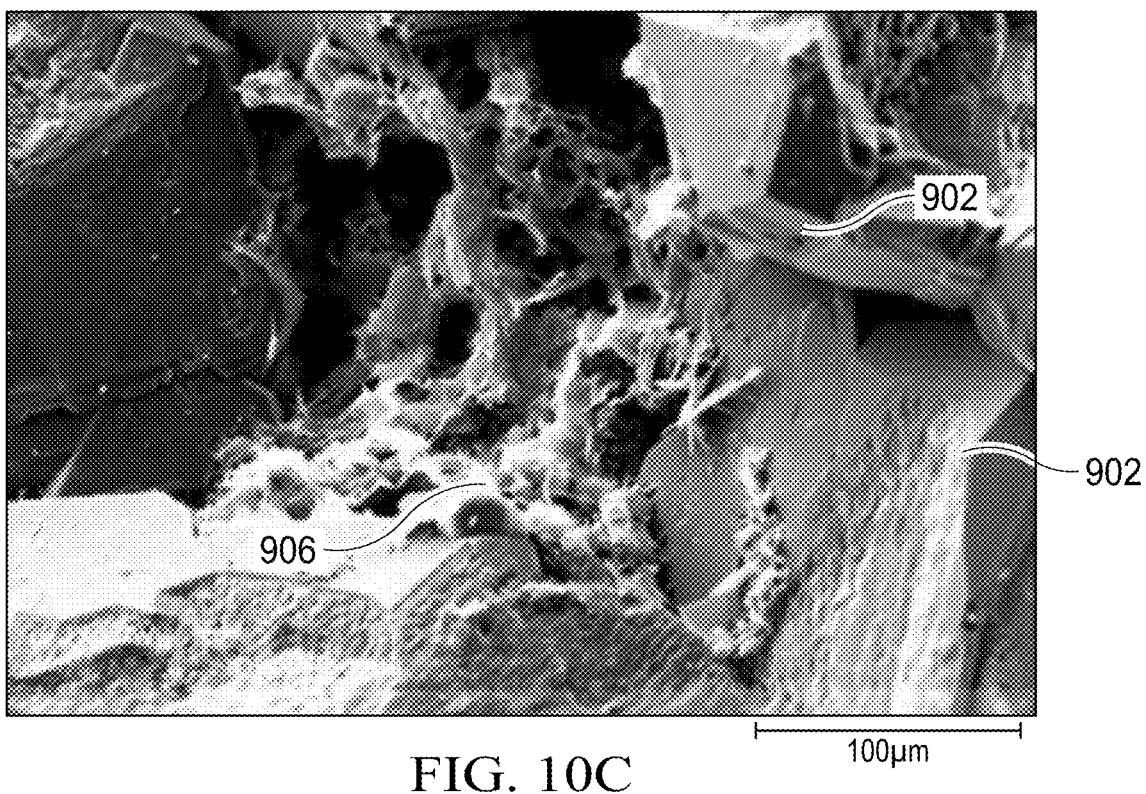
Figure 10D:
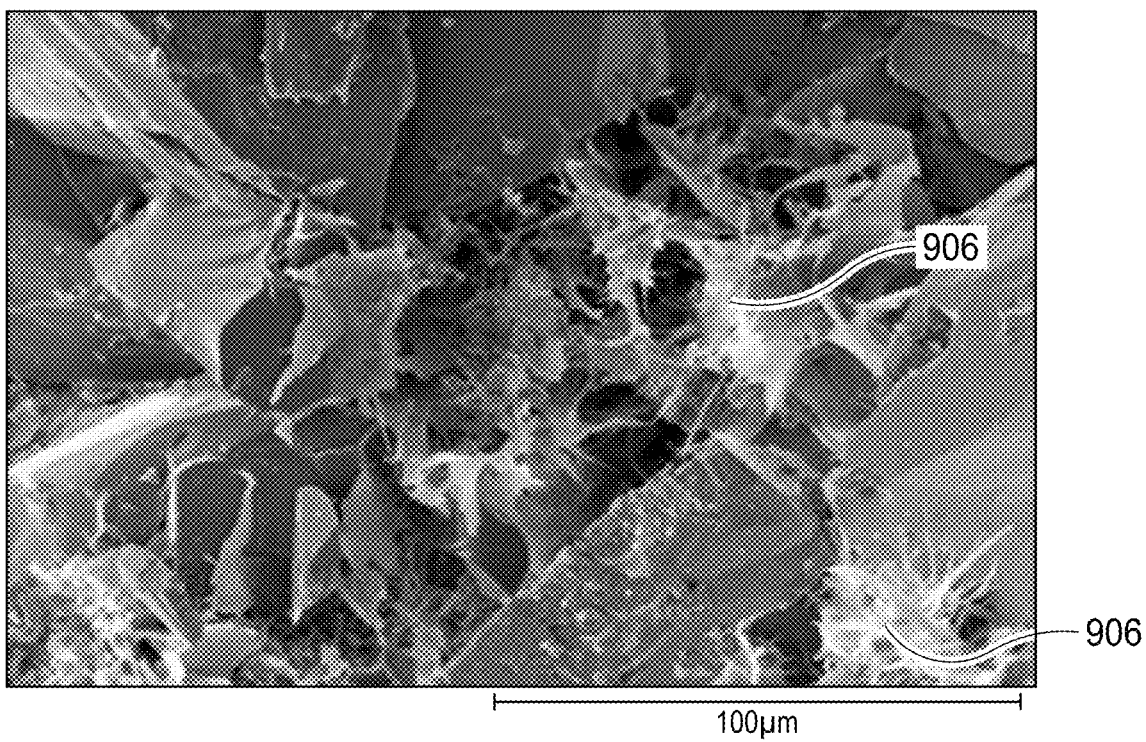
Figure 10E:
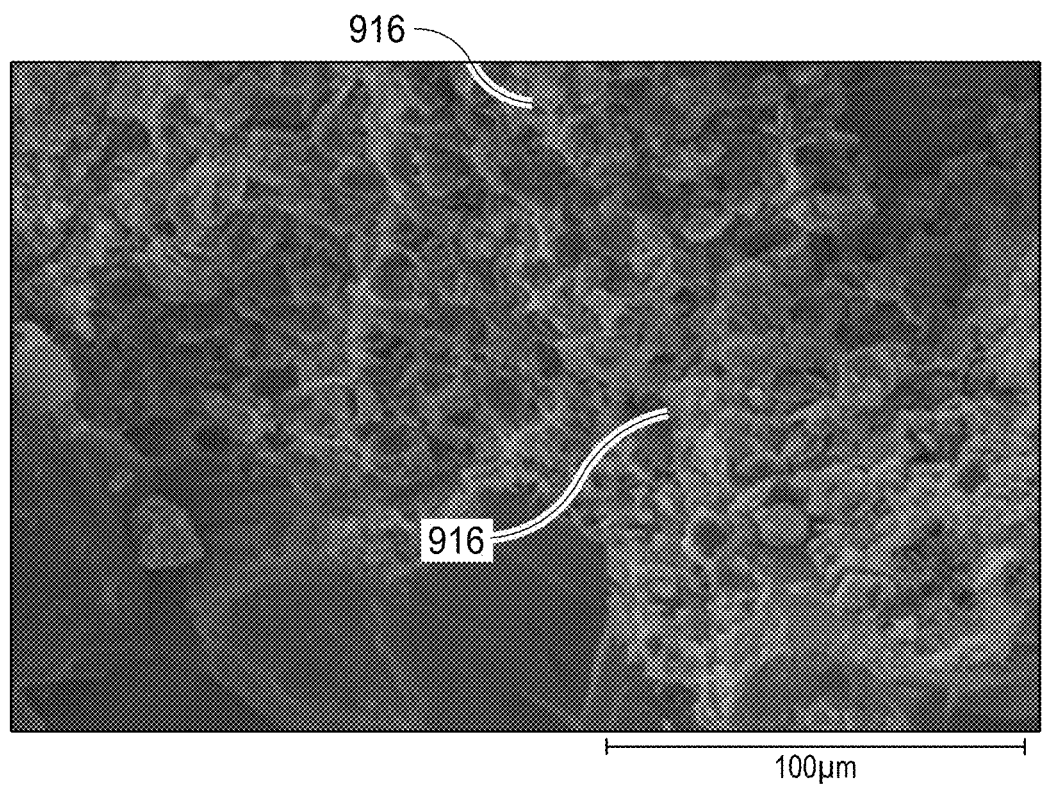
Figure 10F:
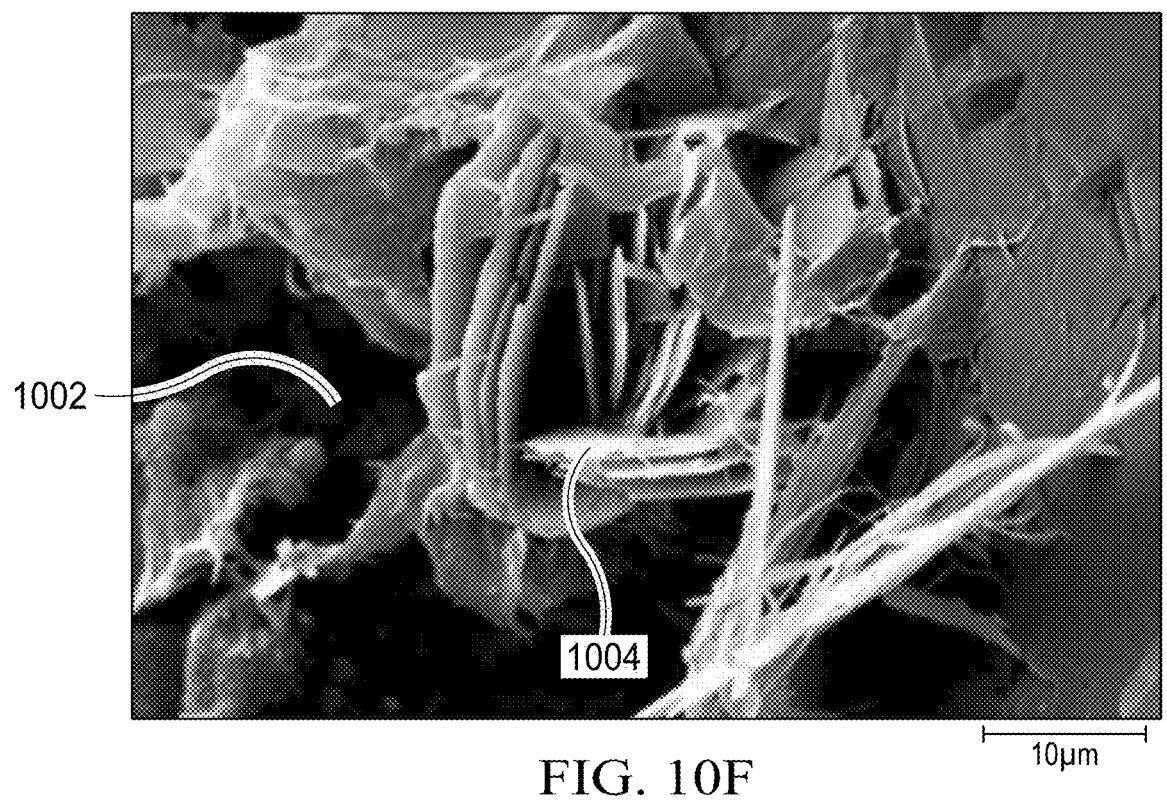

FIGS. 9A-9F show examples of plane polarized light thin section images showing studied sandstone textures and their main components including framework grains and authigenic cements, according to some implementations of the present disclosure. The image in FIG. 9A is a clean sandstone with some quartz overgrowth 902 and porosity 904. The image in FIG. 9B is a sandstone with abundant quartz overgrowth 902 and less porosity 904. The image in FIG. 9C is a sandstone with quartz overgrowth 902, porosity 904 and some illite 906. The image in FIG. 9D is a tight sandstone with some grain coating clay mineral and abundant (syntaxial) quartz overgrowths 908, rounded quartz grains 910, and grain coating clay 912. The image in FIG. 9E is a sandstone with abundant quartz grain 910, quartz overgrowth 902, grain coating clay 912 and booklet kaolinite 914. The image in FIG. 9F is a tight sandstone with abundant quartz overgrowth 902, quartz grain 910 and kaolinite 916.

FIGS. 10A-10F show examples of scanning electric microscope (SEM) images showing studied sandstone three-dimensional (3D) textures and their main components including framework grains (quartz) and authigenic minerals, according to some implementations of the present disclosure. The image in FIG. 10A includes clean sandstone with some quartz overgrowth 902 and pore space 1002. The image in FIG. 10B includes sandstone with abundant quartz overgrowth 902 and minor illite 906. The image in FIG. 10C includes sandstone with abundant quartz overgrowth 902 and minor illite 906. The image in FIG. 10D includes tight sandstone with abundant pore filling illite 906. The image in FIG. 10E includes sandstone with abundant pore filling booklet kaolinite 916. The image in FIG. 10F includes sandstone with pore space 1002 and minor chlorite 1004.

FIG. 11A is an example of a script 1100 that was programmed to assist the diagenetic rock typing processing, according to some implementations of the present disclosure. The script 1100 can be applied to either a single well or multiple wells.

FIG. 11B is an example of a script 1102 that was programmed to assist the one-dimensional (1D) sweet spot index computation and flag process, according to some implementations of the present disclosure. The script 1102 can be applied for either single well or multiple wells.

FIG. 12 is a flowchart of an example of a method 1200 for determining optimized infill locations, target zones, and well placements in a tight gas sandstone reservoir using diagenetic rock typing and ranked sweet spots, according to some implementations of the present disclosure. For clarity of presentation, the description that follows generally describes method 1200 in the context of the other figures in this description. However, it will be understood that method 1200 can be performed, for example, by any suitable system, environment, software, and hardware, or a combination of systems, environments, software, and hardware, as appropriate. In some implementations, various steps of method 1200 can be run in parallel, in combination, in loops, or in any order.

At 1202, total clay and effective porosity (PHIE) values are determined for a tight gas sandstone reservoir using petrophysical evaluation results. As an example, the petrophysical evaluation results for the tight gas sandstone reservoir can include a quartz volume, an orthoclase volume, an illite volume, a kaolinite volume, a chlorite volume, a total porosity, an effective porosity, a gas volume, and a water volume. From 1202, method 1200 proceeds to 1204.

At 1204, regions of the tight gas sandstone reservoir are characterized, including performing diagenetic rock typing for the regions using the total clay and PHIE values, where the diagenetic rock typing reflects porosity/permeability and clay content change. Performing diagenetic rock typing for the regions can include, for example, determining a diagenetic rock type code for each rock sample from a set diagenetic rock type code corresponding to combinations of numeric ranges of the PHIE and total clay values. From 1204, method 1200 proceeds to 1206.

At 1206, sweet spots are determined based on the diagenetic rock typing, where the sweet spots identify well locations and target zones for horizontal drilling.

At 1208, ranked sweet spots are determined by indexing and ranking the sweet spots by category. For example, the sweet spots can include mapping the sweet spot index curve, as described with reference to FIG. 4. The sweet spot index curve can be categorized into varying levels of categories of good, moderate, and poor, based on the index curve values and sandstone frackability. From 1208, method 1200 proceeds to 1210.

At 1210, optimized infill locations, target zones, and well placements are determined in the tight gas sandstone reservoir using the diagenetic rock typing and the ranked sweet spots. After 1210, method 1200 can stop.

In some implementations, method 1200 further include providing information from the results of method 1200 in a graphical user interface presented to a user. Example plots that can be presented to a user (for example, in a GUI) are described with reference to FIGS. 2, 3, and 4. As an example, a plot can be determined that maps rock samples to areas of the plot, wherein points on the plot are plotted relative to an x-axis of effective porosity and a y-axis of total clay, and wherein a color or grayscale of a point is mapped to a gas volume scale. In another example, a plot can be determined that plots results of tight sandstone diagenetic rock typing relative to a depth scale, wherein the results include a quartz volume, an orthoclase volume, a kaolinite volume, an illite volume, and a chlorite volume, a PHIE, a clay content, and a diagenetic rock typing scale. In another example, a plot can be determined that plots a sandstone sweet spot one-dimensional index computation and flagged results relative to a depth scale, wherein the plot includes a diagenetic rock type, a gas volume, a computed sweet spot index curve, and a sweet spot flag block curve.

Figure 13:
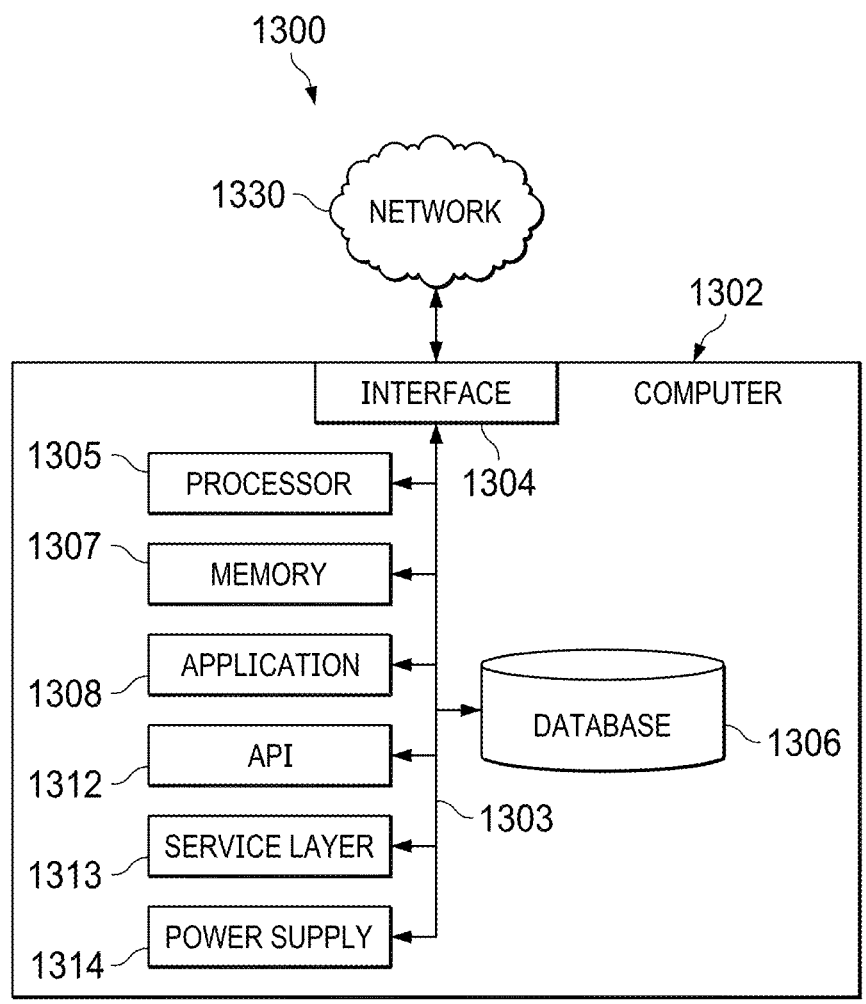
FIG. 13 is a block diagram illustrating an example computer system used to provide computational functionalities associated with described algorithms, methods, functions, processes, flows, and procedures as described in the present disclosure, according to some implementations of the present disclosure.

FIG. 13 is a block diagram of an example computer system 1300 used to provide computational functionalities associated with described algorithms, methods, functions, processes, flows, and procedures described in the present disclosure, according to some implementations of the present disclosure. The illustrated computer 1302 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 1302 can include input devices such as keypads, keyboards, and touch screens that can accept user information. Also, the computer 1302 can include output devices that can convey information associated with the operation of the computer 1302. The information can include digital data, visual data, audio information, or a combination of information. The information can be presented in a graphical user interface (UI) (or GUI).

The computer 1302 can serve in a role as a client, a network component, a server, a database, a persistency, or components of a computer system for performing the subject matter described in the present disclosure. The illustrated computer 1302 is communicably coupled with a network 1330. In some implementations, one or more components of the computer 1302 can be configured to operate within different environments, including cloud-computing-based environments, local environments, global environments, and combinations of environments.

At a top level, the computer 1302 is an electronic computing device operable to receive, transmit, process, store, and manage data and information associated with the described subject matter. According to some implementations, the computer 1302 can also include, or be communicably coupled with, an application server, an email server, a web server, a caching server, a streaming data server, or a combination of servers.

The computer 1302 can receive requests over network 1330 from a client application (for example, executing on another computer 1302). The computer 1302 can respond to the received requests by processing the received requests using software applications. Requests can also be sent to the computer 1302 from internal users (for example, from a command console), external (or third) parties, automated applications, entities, individuals, systems, and computers.

Each of the components of the computer 1302 can communicate using a system bus 1303. In some implementations, any or all of the components of the computer 1302, including hardware or software components, can interface with each other or the interface 1304 (or a combination of both) over the system bus 1303. Interfaces can use an application programming interface (API) 1312, a service layer 1313, or a combination of the API 1312 and service layer 1313. The API 1312 can include specifications for routines, data structures, and object classes. The API 1312 can be either computer-language independent or dependent. The API 1312 can refer to a complete interface, a single function, or a set of APIs.

The service layer 1313 can provide software services to the computer 1302 and other components (whether illustrated or not) that are communicably coupled to the computer 1302. The functionality of the computer 1302 can be accessible for all service consumers using this service layer. Software services, such as those provided by the service layer 1313, can provide reusable, defined functionalities through a defined interface. For example, the interface can be software written in JAVA, C++, or a language providing data in extensible markup language (XML) format. While illustrated as an integrated component of the computer 1302, in alternative implementations, the API 1312 or the service layer 1313 can be stand-alone components in relation to other components of the computer 1302 and other components communicably coupled to the computer 1302. Moreover, any or all parts of the API 1312 or the service layer 1313 can be implemented as child or sub-modules of another software module, enterprise application, or hardware module without departing from the scope of the present disclosure.

The computer 1302 includes an interface 1304. Although illustrated as a single interface 1304 in FIG. 13, two or more interfaces 1304 can be used according to particular needs, desires, or particular implementations of the computer 1302 and the described functionality. The interface 1304 can be used by the computer 1302 for communicating with other systems that are connected to the network 1330 (whether illustrated or not) in a distributed environment. Generally, the interface 1304 can include, or be implemented using, logic encoded in software or hardware (or a combination of software and hardware) operable to communicate with the network 1330. More specifically, the interface 1304 can include software supporting one or more communication protocols associated with communications. As such, the network 1330 or the interface's hardware can be operable to communicate physical signals within and outside of the illustrated computer 1302.

The computer 1302 includes a processor 1305. Although illustrated as a single processor 1305 in FIG. 13, two or more processors 1305 can be used according to particular needs, desires, or particular implementations of the computer 1302 and the described functionality. Generally, the processor 1305 can execute instructions and can manipulate data to perform the operations of the computer 1302, including operations using algorithms, methods, functions, processes, flows, and procedures as described in the present disclosure.

The computer 1302 also includes a database 1306 that can hold data for the computer 1302 and other components connected to the network 1330 (whether illustrated or not). For example, database 1306 can be an in-memory, conventional, or a database storing data consistent with the present disclosure. In some implementations, database 1306 can be a combination of two or more different database types (for example, hybrid in-memory and conventional databases) according to particular needs, desires, or particular implementations of the computer 1302 and the described functionality. Although illustrated as a single database 1306 in FIG. 13, two or more databases (of the same, different, or combination of types) can be used according to particular needs, desires, or particular implementations of the computer 1302 and the described functionality. While database 1306 is illustrated as an internal component of the computer 1302, in alternative implementations, database 1306 can be external to the computer 1302.

The computer 1302 also includes a memory 1307 that can hold data for the computer 1302 or a combination of components connected to the network 1330 (whether illustrated or not). Memory 1307 can store any data consistent with the present disclosure. In some implementations, memory 1307 can be a combination of two or more different types of memory (for example, a combination of semiconductor and magnetic storage) according to particular needs, desires, or particular implementations of the computer 1302 and the described functionality. Although illustrated as a single memory 1307 in FIG. 13, two or more memories 1307 (of the same, different, or combination of types) can be used according to particular needs, desires, or particular implementations of the computer 1302 and the described functionality. While memory 1307 is illustrated as an internal component of the computer 1302, in alternative implementations, memory 1307 can be external to the computer 1302.

The application 1308 can be an algorithmic software engine providing functionality according to particular needs, desires, or particular implementations of the computer 1302 and the described functionality. For example, application 1308 can serve as one or more components, modules, or applications. Further, although illustrated as a single application 1308, the application 1308 can be implemented as multiple applications 1308 on the computer 1302. In addition, although illustrated as internal to the computer 1302, in alternative implementations, the application 1308 can be external to the computer 1302.

The computer 1302 can also include a power supply 1314. The power supply 1314 can include a rechargeable or non-rechargeable battery that can be configured to be either user- or non-user-replaceable. In some implementations, the power supply 1314 can include power-conversion and management circuits, including recharging, standby, and power management functionalities. In some implementations, the power-supply 1314 can include a power plug to allow the computer 1302 to be plugged into a wall socket or a power source to, for example, power the computer 1302 or recharge a rechargeable battery.

There can be any number of computers 1302 associated with, or external to, a computer system containing computer 1302, with each computer 1302 communicating over network 1330. Further, the terms "client," "user," and other appropriate terminology can be used interchangeably, as appropriate, without departing from the scope of the present disclosure. Moreover, the present disclosure contemplates that many users can use one computer 1302 and one user can use multiple computers 1302.

Described implementations of the subject matter can include one or more features, alone or in combination.

For example, in a first implementation, a computer-implemented method includes the following. Total clay, effective porosity (PHIE) values, and gas volume are determined for a tight gas sandstone reservoir characterization using petrophysical evaluation results. Regions of the tight gas sandstone reservoir are characterized, including performing diagenetic rock typing for the regions using the total clay and PHIE values, where the diagenetic rock typing reflects porosity/permeability and clay content change. Sweet spots are determined based on the diagenetic rock typing and gas volume variation. Ranked sweet spots are determined by indexing and ranking the sweet spots by category. Optimized infill drilling locations and target zones are determined, and well placements in the tight gas sandstone reservoir are assisted using the diagenetic rock typing and the ranked sweet spots.

The foregoing and other described implementations can each, optionally, include one or more of the following features:

A first feature, combinable with any of the following features, where the sweet spot (SSP) index curve is a function of diagenetic rock type (DRT) and gas volume (UGAS) given by: $SSP=DRT^3 \cdot UGAS$.

A second feature, combinable with any of the previous or following features, where the sweet spot index curve includes sweet spots that are categorized in varying levels of categories of good, moderate, and poor, based on the values applied to sweet spot index curve.

A third feature, combinable with any of the previous or following features, where the method further includes determining, using the diagenetic rock typing and the ranked sweet spots to optimize intervals for hydraulic fracking.

A fourth feature, combinable with any of the previous or following features, where the petrophysical evaluation results for the tight gas sandstone reservoir include a quartz volume, an orthoclase volume, an illite volume, a kaolinite volume, a chlorite volume, a total porosity, an effective porosity, a gas volume, and a water volume.

A fifth feature, combinable with any of the previous or following features, where performing diagenetic rock typing for the regions includes determining a code for each diagenetic rock type based on the numeric ranges of the PHIE and total clay values.

A sixth feature, combinable with any of the previous or following features, where the method further includes: determining a plot that maps rock samples to areas of the plot, where points on the plot are plotted relative to an x-axis of effective porosity and a y-axis of total clay, and where a color or grayscale of a point is mapped to gas volume scale; and presenting the plot in a graphical user interface.

A seventh feature, combinable with any of the previous or following features, where the method further includes: determining a plot that plots results of tight sandstone diagenetic rock typing relative to a depth scale, where the results include a quartz volume, an orthoclase volume, a kaolinite volume, an illite volume, and a chlorite volume, a PHIE, a clay content, and a diagenetic rock types; and presenting the plot in a graphical user interface.

An eighth feature, combinable with any of the previous or following features, where the method further includes: determining a plot that plots a sandstone sweet spot one-dimensional index computation and flagged results relative to a depth scale, where the plot includes a diagenetic rock type, a gas volume, a computed sweet spot index curve, and a sweet spot flag block curve; and presenting the plot in a graphical user interface.

In a second implementation, a computer-implemented system includes one or more processors and a non-transitory computer-readable storage medium coupled to the one or more processors and storing programming instructions for execution by the one or more processors. The programming instructions instruct the one or more processors to perform operations including the following. Total clay, effective porosity (PHIE) values, and gas volume are determined for a tight gas sandstone reservoir characterization using petrophysical evaluation results. Regions of the tight gas sandstone reservoir are characterized, including performing diagenetic rock typing for the regions using the total clay and PHIE values, where the diagenetic rock typing reflects porosity/permeability and clay content change. Sweet spots are determined based on the diagenetic rock typing and gas volume variation. Ranked sweet spots are determined by indexing and ranking the sweet spots by category. Optimized infill drilling locations and target zones are determined, and well placements in the tight gas sandstone reservoir are assisted using the diagenetic rock typing and the ranked sweet spots.

The foregoing and other described implementations can each, optionally, include one or more of the following features:

A first feature, combinable with any of the following features, where the sweet spot (SSP) index curve is a function of diagenetic rock type (DRT) and gas volume (UGAS) given by: $SSP=DRT^3 \cdot UGAS$.

A second feature, combinable with any of the previous or following features, where the sweet spot index curve includes sweet spots that are categorized in varying levels of categories of good, moderate, and poor, based on the values applied to sweet spot index curve.

A third feature, combinable with any of the previous or following features, where the operations further include determining, using the diagenetic rock typing and the ranked sweet spots to optimize intervals for hydraulic fracking.

A fourth feature, combinable with any of the previous or following features, where the petrophysical evaluation results for the tight gas sandstone reservoir include a quartz volume, an orthoclase volume, an illite volume, a kaolinite volume, a chlorite volume, a total porosity, an effective porosity, a gas volume, and a water volume.

A fifth feature, combinable with any of the previous or following features, where performing diagenetic rock typing for the regions includes determining a code for each diagenetic rock type based on the numeric ranges of the PHIE and total clay values.

A sixth feature, combinable with any of the previous or following features, where the operations further include: determining a plot that maps rock samples to areas of the plot, where points on the plot are plotted relative to an x-axis of effective porosity and a y-axis of total clay, and where a color or grayscale of a point is mapped to gas volume scale; and presenting the plot in a graphical user interface.

A seventh feature, combinable with any of the previous or following features, where the operations further include: determining a plot that plots results of tight sandstone diagenetic rock typing relative to a depth scale, where the results include a quartz volume, an orthoclase volume, a kaolinite volume, an illite volume, and a chlorite volume, a PHIE, a clay content, and a diagenetic rock types; and presenting the plot in a graphical user interface.

An eighth feature, combinable with any of the previous or following features, where the operations further include: determining a plot that plots a sandstone sweet spot one-dimensional index computation and flagged results relative to a depth scale, where the plot includes a diagenetic rock type, a gas volume, a computed sweet spot index curve, and a sweet spot flag block curve; and presenting the plot in a graphical user interface.

In a third implementation, a non-transitory, computer-readable medium stores one or more instructions executable by a computer system to perform operations including the following. Total clay, effective porosity (PHIE) values, and gas volume are determined for a tight gas sandstone reservoir characterization using petrophysical evaluation results. Regions of the tight gas sandstone reservoir are characterized, including performing diagenetic rock typing for the regions using the total clay and PHIE values, where the diagenetic rock typing reflects porosity/permeability and clay content change. Sweet spots are determined based on the diagenetic rock typing and gas volume variation. Ranked sweet spots are determined by indexing and ranking the sweet spots by category. Optimized infill drilling locations and target zones are determined, and well placements in the tight gas sandstone reservoir are assisted using the diagenetic rock typing and the ranked sweet spots.

The foregoing and other described implementations can each, optionally, include one or more of the following features:

A first feature, combinable with any of the following features, where the sweet spot (SSP) index curve is a function of diagenetic rock type (DRT) and gas volume (UGAS) given by: $SSP=DRT^3 \cdot UGAS$.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal. For example, the signal can be a machine-generated electrical, optical, or electromagnetic signal that is generated to encode information for transmission to a suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatuses, devices, and machines for processing data, including by way of example, a programmable processor, a computer, or multiple processors or computers. The apparatus can also include special purpose logic circuitry including, for example, a central processing unit (CPU), a field-programmable gate array (FPGA), or an application-specific integrated circuit (ASIC). In some implementations, the data processing apparatus or special purpose logic circuitry (or a combination of the data processing apparatus or special purpose logic circuitry) can be hardware- or software-based based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, such as LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub-programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory.

Graphics processing units (GPUs) can also be used in combination with CPUs. The GPUs can provide specialized processing that occurs in parallel to processing performed by CPUs. The specialized processing can include artificial intelligence (AI) applications and processing, for example. GPUs can be used in GPU clusters or in multi-GPU computing.

A computer can include, or be operatively coupled to, one or more mass storage devices for storing data. In some implementations, a computer can receive data from, and transfer data to, the mass storage devices including, for example, magnetic, magneto-optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer-readable media (transitory or non-transitory, as appropriate) suitable for storing computer program instructions and data can include all forms of permanent/non-permanent and volatile/non-volatile memory, media, and memory devices. Computer-readable media can include, for example, semiconductor memory devices such as random access memory (RAM), read-only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer-readable media can also include, for example, magnetic devices such as tape, cartridges, cassettes, and internal/removable disks. Computer-readable media can also include magneto-optical disks and optical memory devices and technologies including, for example, digital video disc (DVD), CD-ROM, DVD+/−R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated into, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that the user uses. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch-screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back-end component, for example, as a data server, or that includes a middleware component, for example, an application server. Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations. It should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system including a computer memory interoperably coupled with a hardware processor configured to perform the computer-implemented method or the instructions stored on the non-transitory, computer-readable medium.

What is claimed is:

1. A computer-implemented method, comprising:
   determining, using petrophysical evaluation results, total clay, effective porosity (PHIE) values and gas volume for a tight gas sandstone reservoir;
   characterizing regions of the tight gas sandstone reservoir, including performing diagenetic rock typing for the regions using the total clay and PHIE values, wherein the diagenetic rock typing reflects porosity, permeability, and clay content change;
   determining sweet spots (SSPs) based on the diagenetic rock typing and gas volume variation, wherein an SSP is an area capable of producing gas after hydraulic fracking;
   determining ranked SSPs by indexing and ranking the SSPs by category;
   generating, using at least the ranked SSPs, an SSP index curve as a function of diagenetic rock type (DRT) and gas volume (UGAS) given by SSP=DRT3·UGAS, wherein the SSP index curve represents an SSP index relative to a depth;
   determining optimized infill drilling locations and target zones, and assist well placements in the tight gas sandstone reservoir using the diagenetic rock typing and the ranked SSPs; and
   placing wells in tight gas sandstone reservoirs based on the determined optimized infill drilling locations and the target zones.

2. The computer-implemented method of claim 1, wherein the SSP index curve includes SSPs that are categorized in varying levels of categories of good, moderate, and poor, based on the values applied to the SSP index curve.

3. The computer-implemented method of claim 1, further comprising determining, using the diagenetic rock typing and the ranked SSPs to optimize intervals for hydraulic fracking.

4. The computer-implemented method of claim 1, wherein the petrophysical evaluation results for the tight gas sandstone reservoir include a quartz volume, an orthoclase volume, an illite volume, a kaolinite volume, a chlorite volume, a total porosity, an effective porosity, a gas volume, and a water volume.

5. The computer-implemented method of claim 1, wherein performing diagenetic rock typing for the regions includes determining a code for each diagenetic rock type based on numeric ranges of the PHIE and total clay values.

6. The computer-implemented method of claim 5, further comprising:
   determining a plot that maps rock samples to areas of the plot, wherein points on the plot are plotted relative to an x-axis of effective porosity and a y-axis of total clay, and wherein a color or grayscale of a point is mapped to gas volume scale; and
   presenting the plot in a graphical user interface.

7. The computer-implemented method of claim 1, further comprising:
   determining a plot that plots results of tight sandstone diagenetic rock typing relative to a depth scale, wherein the results include a quartz volume, an orthoclase volume, a kaolinite volume, an illite volume, and a chlorite volume, a PHIE, a clay content, and a diagenetic rock types; and
   presenting the plot in a graphical user interface.

8. The computer-implemented method of claim 1, further comprising:
   determining a plot that plots a sandstone SSP one-dimensional index computation and flagged results relative to a depth scale, wherein the plot includes a diagenetic rock type, a gas volume, an SSP index curve, and an SSP flag block curve, and wherein the SSP flag block curve is a graph of blocks plotted relative to a depth flagging good, moderate, and poor areas of SSPs; and
   presenting the plot in a graphical user interface.

9. A computer-implemented system, comprising:
   one or more data sources of petrophysical evaluation results that have been determined and collected for a tight gas sandstone reservoir;
   one or more graphical user interfaces (GUIs) for interacting with users and presenting information based on an analysis of the petrophysical evaluation results;
   one or more processors; and
   a non-transitory computer-readable storage medium coupled to the one or more processors and storing programming instructions for execution by the one or more processors, the programming instructions instructing the one or more processors to perform operations comprising:
      determining, using the petrophysical evaluation results, total clay and effective porosity (PHIE) values for the tight gas sandstone reservoir;
      characterizing regions of the tight gas sandstone reservoir, including performing diagenetic rock typing for the regions using the total clay and PHIE values, wherein the diagenetic rock typing reflects porosity, permeability, and clay content change;
      determining sweet spots (SSPs) based on the diagenetic rock typing, gas volume variation, and rock frackability, wherein the SSPs identify well locations and target zones for horizontal drilling, and wherein an SSP is an area capable of producing gas after hydraulic fracking;
      determining ranked SSPs by indexing and ranking the SSPs by category;
      generating, using at least the ranked SSPs, an SSP index curve as a function of diagenetic rock type (DRT) and gas volume (UGAS) given by SSP=DRT3·UGAS, wherein the SSP index curve represents an SSP index relative to a depth;
      determining optimized infill locations, target zones for well placements in the tight gas sandstone reservoir using the diagenetic rock typing and the ranked SSPs; and
      placing wells in tight gas sandstone reservoirs based on the determined optimized infill drilling locations and the target zones.

10. The computer-implemented system of claim 9, wherein the SSP index curve includes SSPs that are categorized in varying levels of categories of good, moderate, and poor, based on the values applied to the SSP index curve.

11. The computer-implemented system of claim 9, the operations further comprising determining, using the diagenetic rock typing and the ranked SSPs to optimize intervals for hydraulic fracking.

12. The computer-implemented system of claim 9, wherein the petrophysical evaluation results for the tight gas sandstone reservoir include a quartz volume, an orthoclase volume, an illite volume, a kaolinite volume, a chlorite volume, a total porosity, an effective porosity, a gas volume, and a water volume.

13. The computer-implemented system of claim 9, wherein performing diagenetic rock typing for the regions includes determining a code for each diagenetic rock type based on numeric ranges of the PHIE and total clay values.

14. The computer-implemented system of claim 13, the operations further comprising:
   determining a plot that maps rock samples to areas of the plot, wherein points on the plot are plotted relative to an x-axis of effective porosity and a y-axis of total clay, and wherein a color or grayscale of a point is mapped to gas volume scale; and
   presenting the plot in a graphical user interface.

15. The computer-implemented system of claim 9, the operations further comprising:
   determining a plot that plots results of tight sandstone diagenetic rock typing relative to a depth scale, wherein the results include a quartz volume, an orthoclase volume, a kaolinite volume, an illite volume, and a chlorite volume, a PHIE, a clay content, and a diagenetic rock types; and
   presenting the plot in a graphical user interface.

16. The computer-implemented system of claim 9, the operations further comprising:
   determining a plot that plots a sandstone SSP one-dimensional index computation and flagged results relative to a depth scale, wherein the plot includes a diagenetic rock type, a gas volume, an SSP index curve, and an SSP flag block curve, and wherein the SSP flag block curve is a graph of blocks plotted relative to a depth flagging good, moderate, and poor areas of SSPs; and
   presenting the plot in a graphical user interface.

17. A non-transitory, computer-readable medium storing one or more instructions executable by a computer system to perform operations comprising:
   determining, using petrophysical evaluation results, total clay, effective porosity (PHIE) values and gas volume for a tight gas sandstone reservoir;
   characterizing regions of the tight gas sandstone reservoir, including performing diagenetic rock typing for the regions using the total clay and PHIE values, wherein the diagenetic rock typing reflects porosity, permeability, and clay content change;
   determining sweet spots (SSPs) based on the diagenetic rock typing and gas volume variation, wherein an SSP is an area capable of producing gas after hydraulic fracking;
   determining ranked SSPs by indexing and ranking the SSPs by category;
   generating, using at least the ranked SSPs, an SSP index curve as a function of diagenetic rock type (DRT) and gas volume (UGAS) given by SSP=DRT3·UGAS, wherein the SSP index curve represents an SSP index relative to a depth;
   determining optimized infill drilling locations and target zones, and assist well placements in the tight gas sandstone reservoir using the diagenetic rock typing and the ranked SSPs; and
   placing wells in tight gas sandstone reservoirs based on the determined optimized infill drilling locations and the target zones.

* * * * *